United States Patent [19]

Hebert et al.

[11] Patent Number: 5,356,775
[45] Date of Patent: Oct. 18, 1994

[54] PRIMARY STRUCTURE FOR FUNCTIONAL EXPRESSION FROM COMPLEMENTARY DNA OF A MAMMALIAN ATP-SENSITIVE POTASSIUM CHANNEL

[75] Inventors: Steven C. Hebert, Wellesley; Kevin Ho, Newton, both of Mass.

[73] Assignee: Brigham & Women's Hospital, Boston, Mass.

[21] Appl. No.: 921,178

[22] Filed: Jul. 29, 1992

[51] Int. Cl.$^5$ .................... C12N 15/12; C12N 15/10; C12N 15/63

[52] U.S. Cl. ........................ 435/6; 435/69.1; 435/172.3; 435/320.1; 435/252.3; 435/240.2; 935/11; 935/24; 935/56; 536/23.5

[58] Field of Search ................. 435/69.1, 172.3, 320.1, 435/252.3, 240.2, 6; 536/23.5; 935/11, 24, 56

[56] References Cited

PUBLICATIONS

Zagotta, William et al., "Restoration of Inactivation in Mutants of Shaker Potassium Channels by a Peptide Derived from ShB", *Science* 205:568–571 (Oct. 26, 1990).
Aguilar-Bryan, Lydia et al., "Photoaffinity Labeling and Partial Purification of the β Cell Sulfonylurea Receptor Using a Novel, Biologically Active Glyburide Analog", *J. of Biological Chemistry* 265(14):8218–8224 (1990).
Amoroso, Salvatore et al., "Glucose, Sulfonylureas, and Neurotransmitter Release: Role of ATP-Sensitive K+ Channels", *Science* 247:852–854 (Feb. 16, 1990).
Armstrong, Clay et al., "Inactivation of the Sodium Channel–Gating Current Experiments", *J. of Gen. Physiology* 70:567–590 (1977).
Ashcroft, Frances, "Adenosine 5′-Triphosphate-Sensitive Potassium Channels", *Ann. Rev. Neurosci,* 11:97–118 (1988).
Ashcroft, Francis, "ATP-Sensitive K+ Channels: A Link Between B-Cell Metabolism and Insulin Secretion", *Biochem. Soc. Trans.* 18:109–111 (1990).
Ashcroft, Stephen et al., "Properties and Functions of ATP-Sensitive K-Channels", *Cellular Signalling* 2(3):197–214 (1990).
Atkinson, Nigel et al., "A Component of Calcium-Activated Potassium Channels Encoded by the *Drosophilia slo* Locus", *Science* 253:551–555 (Aug. 2, 1991).
Baker, Michael et al., "A Common Ancestor for Bovine Lens Fiber Major Intrinsic Protein, Soybean Nodulin-26 Protein, and *E. coli* Glycerol Facilitator", *Cell* 60:185–186 (Jan. 26, 1990).
Beneski, Daniel et al., "Covalent Labeling of Protein Components of the Sodium Channel With A Photoactivable Derivative of Scorpion Toxin", *Proc. Natl. Acad. Sci. USA* 77(1):639–643 (Jan. 1980).
Bleich, M. et al., "The Luminal K+ Channel of the Thick Ascending Limb of Henle's Loop", *Pflugers Arc* 415:449–460 (1990).

(List continued on next page.)

Primary Examiner—Christopher S. F. Low
Assistant Examiner—Rebecca Prouty
Attorney, Agent, or Firm—Sterne, Kessler, Goldstein & Fox

[57] ABSTRACT

This invention is directed to the cloning of the gene which encodes an ATP-sensitive K+ channel in rat outer medulla cells, isolated cDNA sequences which encode said ATP-sensitive K+ channels, isolated proteins produced by said cDNA sequences, and agents capable of binding to said proteins. Further included in the invention are methods for identifying other members of the family of ATP-sensitive potassium channels (the ROMK1 family of channel proteins), identifying, isolating, and cloning the genes which encode ROMK1 associated polypeptides, identifying agents capable of binding to other members of the family, modulating expression of said family of ATP-sensitive potassium channels, and modulating the activity of said family of ATP-sensitive potassium channels. Additionally, included in the invention are methods for identifying drugs which function as $K_{ATP}$ channel openers and $K_{ATP}$ channel closers.

10 Claims, 15 Drawing Sheets

OTHER PUBLICATIONS

Brenner, M. B. et al., "Cross-Linking of Human T Cell Receptor Proteins: Association Between the T Cell Idiotype β Subunit and the T3 Glycoprotein Heavy Subunit", *Cell* 40:183–190 (Jan. 1985).

Busch, Andreas et al., "An Amino Acid Mutation In a Potassium Channel That Prevents Inhibition by Protein Kinase C", *Science* 255:1705–1707 (Mar. 27, 1992).

Catterall, William A., "Structure and Function of Voltage-Sensitive Ion Channels", *Science* 242:50–61 (Oct. 7, 1988).

Chin, David et al., "Sequence of the *lon* Gene in *Escherichia coli*", *J. of Biological Chemistry* 263(24):11718–11728 (Aug. 25, 1988).

Chung, Sungkwon et al., "Protein Kinase Activity Closely Associated with a Reconstituted Calcium-Activated Potassium Channel", *Science* 253:560–562 (Aug. 2, 1991).

Collins, Francis, "Cystic Fibrosis: Molecular Biology and Therapeutic Implications", *Science* 256:774–779 (May 8, 1992).

de Weille, Jan et al., "Regulation of ATP-Sensitive K+ Channels In Insulinoma Cells: Activation by Somatostatin and Protein Kinase C and the Role of cAMP", *Proc. Natl. Acad. Sci. USA* 86:2971–2975 (Apr. 1989).

de Weille, J. R. et al., "Pharmacology and Regulation of ATP-Sensitive K+ Channels", *Pflugers Arch* 414 (Suppl 1):S80–S87 (1989).

Dhallan, Ravinder et al., "Primary Structure and Functional Expression of a Cyclic Nucleotide-Activated Channel from Olfactory Neurons", *Nature* 347:184–187 (Sep. 13, 1990).

Ding, Ruchuang et al., "Depletion of Poly(ADP-ribose) Polymerase by Antisense RNA Expression Results in a Delay in DNA Strand Break Rejoining", *J. of Biological Chemistry* 267(18):12804–12812 (Jun. 25, 1992).

Durell, Stewart et al., "Atomic Scale Structure and Functional Models of Voltage-Gated Potassium Channels", *Biophys. J.* 62:238–250 (1992).

Escande, D., "The Pharmacology of ATP-Sensitive K+ Channels In the Heart", *Pflugers Arch* 414 (Suppl 1):S93–S98 (1989).

Findlay, Ian, "ATP-Sensitive K+ Channels In Rat Ventricular Myocytes Are Blocked and Inactivated by Internal Divalent Cations", *Pflüers Arch* 410:313–320 (1987).

Hartmann, Enno et al., "Predicting the Orientation of Eukaryotic Membrane-Spanning Proteins", *Proc. Natl. Acad. Sci. USA* 86:5786–5790 (Aug. 1989).

Hartmann, Hali et al., "Exchange of Conduction Pathways Between Two Related K+ Channels", *Science* 251:942–944 (Feb. 22, 1991).

Hartshorne, Robert et al., "The Sodium Channel from Rat Brain", *J. of Biological Chemistry* 259(3):1667–1675 (Feb. 10, 1984).

Hoshi, Toshinori et al., "Biophysical and Molecular Mechanisms of *Shaker* Potassium Channel Inactivation", *Science* 250:533–538 (Oct. 26, 1990).

Hyde, Stephen et al., "Structural Model of ATP-Binding Proteins Associated With Cystic Fibrosis, Multidrug Resistance and Bacterial Transport", *Nature* 346:362–365 (Jul. 26, 1990).

Jan, Lily Yeh et al., "Tracing the Roots of Ion Channels", *Cell* 69:715–718 (May 29, 1992).

Jan, Lily Yeh et al., "A Superfamily of Ion Channels", *Nature* 345:672 (Jun. 21, 1990).

Kasprzak, Andrzej et al., "Location of a Contact Site Between Actin and Myosin in the Three-Dimensional Strucutre of the Acto-S1 Complex", *Biochemistry* 28:9230–9238 (1989).

Kaupp, U. Benjamin et al., "Primary Structure and Fuctional Expression from Complementary DNA of the Rod Photoreceptor Cyclic GMP-Gated Channel", *Nature* 342:762–766 (Dec. 14, 1989).

Kirsch, G. E. et al., "A Single Nonpolar Residue in the Deep Pore of Related K+ Channels Acts as a K+:Rb+ Conductance Switch", *Biophys. J.* 62:136–144 (1992).

Kozak, Marilyn, "Structural Features in Eukaryotic mRNAs That Modulate the Initiation of Translation", *J. of Biological Chemistry* 266(30):19867–19870 (Oct. 25, 1991).

Kunzelmann, Karl et al., "Characterization of Potassium Channels in Respiratory Cells", *Pflugers Arch* 414:297–303 (1989).

Lang, F. et al., "Potassium Channels in Renal Epithelial Transport Regulation", *Physiological Reviews* 72(1):1–32 (Jan. 1992).

Liman, Emily et al., "Voltage-Sensing Residues in the (List continued on next page.)

OTHER PUBLICATIONS

S4 Region of a Mammalian K+ Channel", *Nature* 353:752–756 (Oct. 24, 1991).

MacKinnon, Roderick et al., "Mutations Affecting TEA Blockage and Ion Permeation in Voltage-Activated K+ Channels", *Science* 250:276–279 (Oct. 1990).

MacKinnon, Roderick et al., "Mapping the Receptor Site for Charybdotoxin, a Pore-Blocking Potassium Channel Inhibitor", *Neuron* 5:767–771 (Dec. 1990).

MacKinnon, Roderick et al., "Mutant Potassium Channels with Altered Binding of Charybdotoxin, a Pore-Blocking Peptide Inhibitor", *Science* 245:1382–1385 (Sep. 22, 1989).

Manley, James, "Polyadenylation of mRNA Precursors", *Biochimica et Biophysica Acta* 950:1–12 (1988).

Miller, Richard, "Voltage-Sensitive $Ca^{2+}$ Channels", *J. of Biological Chemistry* 267(3):1403–1406 (Jan. 25, 1992).

Miller, Christopher "1990: Annus Mirabilis of Potassium Channels", *Science* 252:1092∝1096 (May 24, 1991).

Nichols, C. G. et al., "Adenosine Triphosphate-Sensitive Potassium Channels in the Cardiovascular System", *Am. J. Physiol.* 261:H1675–H1686 (1991).

Nichols, C. G. et al., "ATP Dependence of $K_{ATP}$ Channel Kinetics in Isolated Membrane Patches from Rat Ventricle", *Biophys. J.* 60:1164–1177 (Nov. 1991).

Noma, A., "ATP-Regulated K+ Channels in Cardiac Muscle", *Nature* 305:147–148 (Sep. 8, 1983).

Oettgen, Hans et al., "A T3-Like Protein Complex Associated with the Antigen Receptor On Murine T Cells", *Nature* 320:272–275 (Mar. 20, 1986).

Papazian, Diane et al., "Alternation of Voltage-Dependence of *Shaker* Potassium Channel By Mutations in the S4 Sequence", *Nature* 349:305–310 (Jan. 24, 1991).

Pearson, Richard et al., "Protein Kinase Phosphorylation Site Sequences and Consensus Specificity Motifs: Tabulations", *Methods In Enzymology* 200:62–81 (1991).

Perney, Teresa et al., "The Molecular Biology of K+ Channels", *Current Opinion in Cell Biology* 3:663–670 (1991).

Qin, Dayi et al., "Kinetics of ATP-Sensitive K+ Channel Revealed with Oil-Gate Concentration Jump Method", *Am. J. Physiol.* 257:H1624–H1633 (1989).

Rehm, Hubert et al., "Dedrotoxin-Binding Brain Membrane Protein Displays a K+ Channel Activity That Is Stimulated by both cAMP-Dependent and Endogenous Phosphorylations", *Biochemistry* 28:6455–6460 (1989).

Reinhart, Peter et al., "Modulator of Calcium-Activated Potassium Channels from Rat Brain by Protein Kinase A and Phosphatase 2A", *The Journal of Neuroscience* 11(6):1627–1635 (Jun. 1991).

Ribalet, B. et al., "ATP Mediates Both Activation and Inhibition of K(ATP) Channel Activity Via cAMP-Dependent Protein Kinase in Insulin-Secreting Cell Lines", *J. Gen. Physiol.* 94:693–717 (Oct. 1989).

Riordan, John et al., "Identification of the Cystic Fibrosis Gene: Cloning and Characterization of Complementary DNA", *Science* 245:1066–1073 (Sep. 8, 1989).

Rossie, Sandra et al., "Identification of an Intracellular Domain of the Sodium Channel Having Multiple cAMP-Dependent Phosphorylation Sites", *The Journal of Biological Chemistry* 262(36):17530–17535 (Dec. 25, 1987).

Sanguinetti, Michael, "Modulation of Potassium Channels by Antiarrhythmic and Antihypertensive Drugs", *Hypertension 1 19(3):228–236 (Mar. 1992).*

Saraste, Matti et al., "The P-Loop-A Common Motif in ATP- and GTP-Binding Proteins", *TIBS* 15:430–434 (Nov. 1990).

Stühmer, W., "Structure-Function Studies of Voltage-Gated Ion Channels", *Annu. Rev. Biophys. Biophys. Chem.* 20:65–78 (1991).

Swanson, Richard et al., "Cloning and Expression of cDNA and Genomic Clones Encoding Three Delayed Rectifier Potassium Channels in Rat Brain", *Neuron* 4:929–939 (Jun. 1990).

Swope, Sheridan et al., "Phosphorylation of Ligand-Gated Ion Channels: A Possible Mode of Synaptic Plasticity", *The FASEB Journal* 6:2514–2523 (May 1992).

Takano, M. et al., "ATP-Dependent Decay and Recovery of K+ Channels in Guinea Pig Cardiac Myocytes", *Am. J. Physiol.* 258:H45–H50 (1990).

Takumi, Toru et al., "Cloning of a Membrane Protein That Induces a Slow Voltage-Gated Potassium Current", *Science* 242:1042–1045 (Nov. 18, 1988).

Trube, G. et al., in *Secretion and Its Control*, G. S. Oxford and C. M. Armstrong, eds. (Rockefeller University Press, New York, 1989), vol. 44, pp. 84–95.

(List continued on next page.)

OTHER PUBLICATIONS

Tsuura, Yoshiyuki et al., "Impaired glucose Sensitivity of ATP-Sensitive K+ Channels in Pancreatic β-Cells in Streptozotocin-Induced NIDDM Rats", *Diabetes* 41:861-865 (Jul. 1992).

Walker, John et al., "Distantly Related Sequences in the α- and β-Subunits of ATP Synthase, Myosin, Kinases and Other ATP-Requiring Enzymes and a Common Nucleotide Binding Fold", *The EMBO Journal* 1(8):945-951 (1982).

Walsh, Kenneth et al., "Regulation of a Heart Potassium Channel by Protein Kinase A and C", *Science* 242:67-69 (Oct. 7, 1988).

Wang, Wenhui et al., "Dual Effect of Adenosine Triphosphate on the Apical Small Conductance K+ Channel of the Rat Cortical Collecting Duct", *J. Gen. Physiol.* 98:35-61 (Jul. 1991).

Wang, Wenhui et al., "Regulation of Small-Conductance K+ Channel in Apical Membrane of Rat Cortical Collecting Tubule", *Am. J. Physiol.* 259:F494-F502 (1990).

Wang, Wenhui et al., "A Potassium Channel in the Apical Membrane of Rabbit Thick Ascending Limb of Henle's Loop", *Am. J. Physiol.* 258:F244-F253 (1990).

Warmke, Jeffrey et al., "A Distinct Potassium Channel Polypeptide Encoded by the *Drosophila eag* Locus", *Science* 252:1560-1562 (Jun. 14, 1991).

Wei, Aguan et al., "K+ Current Diversity Is Produced by an Extended Gene Family Conserved in *Drosophila* and Mouse", *Science* 248:599-603 (May 4, 1990).

Weston, A. H., "Smooth Muscle K+ Channel Openers; Their Pharmacology and Clinical Potential", *Pflugers Arch 414 (Suppl 1)*:S99-S105 (1989).

Wistow, Graeme et al., "Tandem Sequence Repeats in Transmembrane Channel Proteins", *TIBS* 16:170-171 (May 1991).

Wollheim, Claes et al., "Activators by Protein Kinase C Depolarize Insulin-Secreting Cells By Closing K+ Channels", *The EMBO Journal* 7(8):2443-2449 (1988).

Yellen, Gary et al., "Mutations Affecting Internal TEA Blockade Identify the Probable Pore-Forming Region of a K+ Channel", *Science* 251:939-942 (Feb. 22, 1991).

Yool, Andrea et al., "Alteration of Ionic Selectivity of a K+ Channel By Mutation of the H5 Region", *Nature* 349:700-704 (Feb. 21, 1991).

A. Belyavsky et al. Nuc. Acids. Res. 17(8)2919-2932 (Apr. 1989).

M. P. Deutscher (ed) "Guide to Protein Purification" Meth. in Enzymol. vol. 182 pp. 602-613 and 738-751 (1990).

S. L. Berger et al. (eds.) "Guide to Molecular Cloning Techniques" Meth. in Enzymol. vol. 152 pp. 393-399, 415-423, 432-447, 661-704 (1987).

J. Sambrook et al. (eds.) "Molecular Cloning: A Laboratory Manual" Cold Spring Harbor Laboratory Press Chpts. 16 & 17 (Oct. 16, 1989).

```
CAATCACACA ACTCCACTCG AGTTAGCCAT TGAAAGCCAA TGCAAGTAAA TGTCATTCCA                    60

AAGCTTAAGA TTCATTAAGG TGGGCCTAAA AGAAGACAGC TGCTGTGCAG ACAACGTCGA                   120

ACAAGCACCA CTTGCTTGCT TTGCCCAGC ATG GGC GCT TCG GAA CGG AGT GTG                    173
                                Met Gly Ala Ser Glu Arg Ser Val
                                 1           @   5

TTC AGA GTG CTG ATC AGG GCA CTG ACA GAA AGG ATG TTC AAA CAC CTC                    221
Phe Arg Val Leu Ile Arg Ala Leu Thr Glu Arg Met Phe Lys His Leu
     10              15   @           20

CGA AGA TGG TTT ATC ACT CAC ATA TTT GGG CGT TCC CGG CAA CGG GCA                    269
Arg Arg Trp Phe Ile Thr His Ile Phe Gly Arg Ser Arg Gln Arg Ala
 25          30              35                   40

AGG CTG GTC TCT AAA GAA GGA AGA TGT AAC ATC GAG TTT GGC AAT GTG                    317
Arg Leu Val Ser Lys Glu Gly Arg Cys Asn Ile Glu Phe Gly Asn Val
         #   45              50              55

GAT GCA CAG TCA AGG TTT ATA TTC TTT GTG GAC ATC TGG ACA ACT GTG                    365
Asp Ala Gln Ser Arg Phe Ile Phe Phe Val Asp Ile Trp Thr Thr Val
             60              65              70

CTG GAC CTG AAA TGG AGG TAC AAA ATG ACC GTG TTC ATC ACA GCC TTC                    413
Leu Asp Leu Lys Trp Arg Tyr Lys Met Thr Val Phe Ile Thr Ala Phe
         75              80   MI      85

TTG GGG AGT TGG TTC CTC TTT GGT CTC CTG TGG TAT GTC GTA GCG TAT                    461
Leu Gly Ser Trp Phe Leu Phe Gly Leu Leu Trp Tyr Val Val Ala Tyr
         90          95              100

GTT CAT AAG GAC CTC CCA GAG TTC TAC CCG CCT GAC AAC CGC ACT CCT                    509
Val His Lys Asp Leu Pro Glu Phe Tyr Pro Pro Asp Asn Arg Thr Pro
105         110             115             120

TGT GTG GAG AAC ATT AAT GGC ATG ACT TCA GCC TTT CTG TTT TCT CTA                    557
Cys Val Glu Asn Ile Asn Gly Met Thr Ser Ala Phe Leu Phe Ser Leu
             * 125            130             135
                                   H5-like GAG ACT CAA GTG ACC ATA GGT TAC GGA TTC AGG TTT GTG ACA GAA CAG                    605
Glu Thr Gln Val Thr Ile Gly Tyr Gly Phe Arg Phe Val Thr Glu Gln
            140             145             150

TGC GCC ACT GCC ATT TTC CTG CTT ATC TTC CAG TCT ATT CTT GGA GTG                    653
Cys Ala Thr Ala Ile Phe Leu Leu Ile Phe Gln Ser Ile Leu Gly Val
     155 M2         160             165
```

FIG.3A

```
ATC ATC AAT TCC TTC ATG TGT GGT GCC ATT TTA GCC AAG ATC TCT AGA       701
Ile Ile Asn Ser Phe Met Cys Gly Ala Ile Leu Ala Lys Ile Ser Arg
    170             175                 180         @

CCC AAA AAA CGT GCT AAA ACC ATT ACG TTC AGC AAG AAT GCG GTG ATC       749
Pro Lys Lys Arg Ala Lys Thr Ile Thr Phe Ser Lys Asn Ala Val Ile
185                 190 @       @       195                 200

AGC AAG CGT GGC GGG AAG CTC TGC CTC CTC ATC CGA GTG GCC AAT CTT       797
Ser Lys Arg Gly Gly Lys Leu Cys Leu Leu Ile Arg Val Ala Asn Leu
                    205             210             215

AGG AAG AGC CTT CTG ATT GGC AGC CAC ATA TAT GGC AAG CTT CTA AAG       845
Arg Lys Ser Leu Leu Ile Gly Ser His Ile Tyr Gly Lys Leu Leu Lys
         #   220             225             230
                                    WALKER TYPE A
ACA ACC ATC ACT CCT GAA GGC GAG ACC ATC ATT TTG GAT CAG ACC AAC       893
Thr Thr Ile Thr Pro Glu Gly Glu Thr Ile Ile Leu Asp Gln Thr Asn
            235             240 @           245

ATC AAC TTT GTC GTC GAC GCT GGC AAT GAA AAT TTG TTC TTC ATA TCC       941
Ile Asn Phe Val Val Asp Ala Gly Asn Glu Asn Leu Phe Phe Ile Ser
        250             255             260

CCA CTG ACG ATC TAC CAC ATT ATT GAC CAC AAC AGC CCT TTC TTC CAC       989
Pro Leu Thr Ile Tyr His Ile Ile Asp His Asn Ser Pro Phe Phe His
265             270             275                 280

ATG GCA GCA GAA ACT CTT TCC CAA CAG GAC TTT GAG CTG GTG GTC TTT      1037
Met Ala Ala Glu Thr Leu Ser Gln Gln Asp Phe Glu Leu Val Val Phe
                    285             290             295
                                                POSSIBLE WALKER
TTA GAT GGC ACA GTG GAA TCC ACC AGT GCA ACC TGC CAG GTC CGC ACG      1085
Leu Asp Gly Thr Val Glu Ser Thr Ser Ala Thr Cys Gln Val Arg Thr
            300             305             310
TYPE B
TCA TAC GTC CCA GAG GAG GTG CTT TGG GGC TAC CGT TTC GTT CCT ATT      1133
Ser Tyr Val Pro Glu Glu Val Leu Trp Gly Tyr Arg Phe Val Pro Ile
  #      315             320             325

GTG TCC AAG ACC AAG GAA GGG AAA TAC CGA GTT GAT TTT CAT AAC TTC      1181
Val Ser Lys Thr Lys Glu Gly Lys Tyr Arg Val Asp Phe His Asn Phe
    330             335             340
```

FIG.3B

```
GGT AAG ACA GTG GAA GTG GAG ACC CCT CAC TGT GCC ATG TGC CTC TAT     1229
Gly Lys Thr Val Glu Val Glu Thr Pro His Cys Ala Met Cys Leu Tyr
345             350             355             360

AAT GAG AAA GAT GCC AGG GCC AGG ATG AAG AGA GGC TAT GAC AAC CCT     1277
Asn Glu Lys Asp Ala Arg Ala Arg Met Lys Arg Gly Tyr Asp Asn Pro
                365             370             375

AAC TTT GTC TTG TCA GAA GTT GAT GAA ACG GAC GAC ACC CAG ATG         1322
Asn Phe Val Leu Ser Glu Val Asp Glu Thr Asp Asp Thr Gln Met
            380             385             390

TAGCAGTGGC TTTTCCACCT ACAAAAAGCC TCCCAAGGAC CTAAGGGTTG ACTGTGTTCA   1382

GAAGCATCTG ACGGGGGTCT GAAAGCAGGA TGAGAACATG CGAAATCTGC TAGCACAGTC   1442

ACCCCTGAAC CCCAGGGCTA TGGTTCTACA AGACACATAG CTCTATAAGG CTGCATACGG   1502

TGCATGCATG TGAATGAAAC TGTGGAAGCC AAAGGGGCCC ACTTGGATCC TCACTATGAC   1562

TGTGTAAGCT CATATCGTGT TGATGGAAAC AAAGTCATTC AAGGACAAAA CTTAGGAGCT   1622

TTAGAAAGCT TCAGGAACTA GCCACATTTC CTGTTTGATT CTATGGATGA GAAAGATGCC   1682

ATTTTTATCT TAAAGTAGAC TTCTATCAAT GGAAAATCTG CCCTCTGCGC TGGGAAGTGA   1742

GCCAGCCAAT CAGTGACAAT AAGAGACTGT CATACAAAGA ATCAGTAAAG ACTCTAACCT   1802

TCTCAAGCTC TGGTGTTTGA AGCCTTTGTC TGAGTCTGGG TCCATGCTTC AGAAGGGGTA   1862

AGGTGACATC CACTGACTGT ACCTCTCTGA ACCCAAGGTA CAGAAGAACA GGAAGCCCCA   1922

ATCAACTTCA TAATCAACCC AGATGCTGCA GCCCATACAG AATTTGGCCT GAATGATTTC   1982

CTGTGGAGCA TTAAATGGAG GCCAAGTCCA CTCTTTAGAT ATTAAATGAA TATTCTTTTG   2042

CAAAGGAAAA AAAAAAAAAA AAAAAAA                                      2069
```

FIG.3C

H5 Homology

```
Shaker A    D A F W W A V V T M T T V G Y G D M T P V G F W G
RCK4        D A F W W A V V T M T T V G Y G D M K P I T V G G Shal 2      A A F W Y T I V T M T T L G Y G D M V P E T I A G
mShal       A A F W Y T I V T M T T L G Y G D M V P S T I A G Shab 11     E A F W W A G I T M T T V G Y G D I C P T T A L G
Drk1        A S F W W A T I T M T T V G Y G D I Y P K T L L G Shaw 2      L G L W W A L V T M T T V G Y G D M A P K T Y T G
NGK2        I G F W W A V V T M T T L G Y G D M Y P Q T W S G Eag         T A L Y F T M T C M T S V G F G N V A A E T D N E
Slo         T C V Y F L I V T M S T V G Y G D V Y C E T V L G
ROMK1       S A F L F S L E T Q V T I G Y G F R F V T E Q C A
```

FIG.5A

S4 Homology

```
cGMP-gated  Y P E I R L N R L L R I S R M -         F E F F Q R T E T
Na+brain I  P T L F R V T R L A R I G R I -         L R L I K G A K G
ROMK1       D A Q S R F I F F V D I W T T V         L D L K W R Y K M
Shaker A    L A I L R V I R L V R V F R I -         F K L S R H S K G
Shab 11     D Q F Q D V R R V V Q V F R IHR1LRV    L K L A R H S T G
Shaw2       L E N A D I L E F F S T I I R I HRL F  K L T R H S S G
```

FIG.5B

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
( A ) LENGTH: 2069 base pairs
( B ) TYPE: nucleic acid
( C ) STRANDEDNESS: both
( D ) TOPOLOGY: linear ( i i ) MOLECULE TYPE: cDNA ( i x ) FEATURE:
( A ) NAME/KEY: CDS
( B ) LOCATION: 150..1322

( x i ) SEQUENCE DESCRIPTION: SEQ ID NO:1:

```
CAATCACACA ACTCCACTCG AGTTAGCCAT TGAAAGCCAA TGCAAGTAAA TGTCATTCCA        60

AAGCTTAAGA TTCATTAAGG TGGGCCTAAA AGAAGACAGC TGCTGTGCAG ACAACGTCGA       120

ACAAGCACCA CTTGCTTGCT TTGCCCAGC ATG GGC GCT TCG GAA CGG AGT GTG        173
                                 Met Gly Ala Ser Glu Arg Ser Val
                                  1               5

TTC AGA GTG CTG ATC AGG GCA CTG ACA GAA AGG ATG TTC AAA CAC CTC        221
Phe Arg Val Leu Ile Arg Ala Leu Thr Glu Arg Met Phe Lys His Leu
     10              15                  20

CGA AGA TGG TTT ATC ACT CAC ATA TTT GGG CGT TCC CGG CAA CGG GCA        269
Arg Arg Trp Phe Ile Thr His Ile Phe Gly Arg Ser Arg Gln Arg Ala
 25              30                  35                  40

AGG CTG GTC TCT AAA GAA GGA AGA TGT AAC ATC GAG TTT GGC AAT GTG        317
Arg Leu Val Ser Lys Glu Gly Arg Cys Asn Ile Glu Phe Gly Asn Val
             45                  50                  55

GAT GCA CAG TCA AGG TTT ATA TTC TTT GTG GAC ATC TGG ACA ACT GTG        365
Asp Ala Gln Ser Arg Phe Ile Phe Phe Val Asp Ile Trp Thr Thr Val
                 60                  65                  70

CTG GAC CTG AAA TGG AGG TAC AAA ATG ACC GTG TTC ATC ACA GCC TTC        413
Leu Asp Leu Lys Trp Arg Tyr Lys Met Thr Val Phe Ile Thr Ala Phe
         75                  80                  85

TTG GGG AGT TGG TTC CTC TTT GGT CTC CTG TGG TAT GTC GTA GCG TAT        461
Leu Gly Ser Trp Phe Leu Phe Gly Leu Leu Trp Tyr Val Val Ala Tyr
     90                  95                 100

GTT CAT AAG GAC CTC CCA GAG TTC TAC CCG CCT GAC AAC CGC ACT CCT        509
Val His Lys Asp Leu Pro Glu Phe Tyr Pro Pro Asp Asn Arg Thr Pro
105                 110                 115                 120

TGT GTG GAG AAC ATT AAT GGC ATG ACT TCA GCC TTT CTG TTT TCT CTA        557
Cys Val Glu Asn Ile Asn Gly Met Thr Ser Ala Phe Leu Phe Ser Leu
                125                 130                 135

GAG ACT CAA GTG ACC ATA GGT TAC GGA TTC AGG TTT GTG ACA GAA CAG        605
Glu Thr Gln Val Thr Ile Gly Tyr Gly Phe Arg Phe Val Thr Glu Gln
            140                 145                 150

TGC GCC ACT GCC ATT TTC CTG CTT ATC TTC CAG TCT ATT CTT GGA GTG        653
Cys Ala Thr Ala Ile Phe Leu Leu Ile Phe Gln Ser Ile Leu Gly Val
            155                 160                 165

ATC ATC AAT TCC TTC ATG TGT GGT GCC ATT TTA GCC AAG ATC TCT AGA        701
Ile Ile Asn Ser Phe Met Cys Gly Ala Ile Leu Ala Lys Ile Ser Arg
        170                 175                 180

CCC AAA AAA CGT GCT AAA ACC ATT ACG TTC AGC AAG AAT GCG GTG ATC        749
Pro Lys Lys Arg Ala Lys Thr Ile Thr Phe Ser Lys Asn Ala Val Ile
185                 190                 195                 200

AGC AAG CGT GGC GGG AAG CTC TGC CTC CTC ATC CGA GTG GCC AAT CTT        797
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| Ser | Lys | Arg | Gly | Gly<br>205 | Lys | Leu | Cys | Leu | Leu<br>210 | Ile | Arg | Val | Ala | Asn<br>215 | Leu | |
| AGG | AAG | AGC | CTT | CTG | ATT | GGC | AGC | CAC | ATA | TAT | GGC | AAG | CTT | CTA | AAG | 845 |
| Arg | Lys | Ser | Leu<br>220 | Leu | Ile | Gly | Ser | His<br>225 | Ile | Tyr | Gly | Lys | Leu<br>230 | Leu | Lys | |
| ACA | ACC | ATC | ACT | CCT | GAA | GGC | GAG | ACC | ATC | ATT | TTG | GAT | CAG | ACC | AAC | 893 |
| Thr | Thr | Ile<br>235 | Thr | Pro | Glu | Gly | Glu<br>240 | Thr | Ile | Ile | Leu | Asp<br>245 | Gln | Thr | Asn | |
| ATC | AAC | TTT | GTC | GTC | GAC | GCT | GGC | AAT | GAA | AAT | TTG | TTC | TTC | ATA | TCC | 941 |
| Ile | Asn | Phe<br>250 | Val | Val | Asp | Ala | Gly<br>255 | Asn | Glu | Asn | Leu | Phe<br>260 | Phe | Ile | Ser | |
| CCA | CTG | ACG | ATC | TAC | CAC | ATT | ATT | GAC | CAC | AAC | AGC | CCT | TTC | TTC | CAC | 989 |
| Pro<br>265 | Leu | Thr | Ile | Tyr | His<br>270 | Ile | Ile | Asp | His | Asn<br>275 | Ser | Pro | Phe | Phe | His<br>280 | |
| ATG | GCA | GCA | GAA | ACT | CTT | TCC | CAA | CAG | GAC | TTT | GAG | CTG | GTG | GTC | TTT | 1037 |
| Met | Ala | Ala | Glu | Thr<br>285 | Leu | Ser | Gln | Gln | Asp<br>290 | Phe | Glu | Leu | Val | Val<br>295 | Phe | |
| TTA | GAT | GGC | ACA | GTG | GAA | TCC | ACC | AGT | GCA | ACC | TGC | CAG | GTC | CGC | ACG | 1085 |
| Leu | Asp | Gly | Thr<br>300 | Val | Glu | Ser | Thr | Ser<br>305 | Ala | Thr | Cys | Gln | Val<br>310 | Arg | Thr | |
| TCA | TAC | GTC | CCA | GAG | GAG | GTG | CTT | TGG | GGC | TAC | CGT | TTC | GTT | CCT | ATT | 1133 |
| Ser | Tyr | Val<br>315 | Pro | Glu | Glu | Val | Leu<br>320 | Trp | Gly | Tyr | Arg | Phe<br>325 | Val | Pro | Ile | |
| GTG | TCC | AAG | ACC | AAG | GAA | GGG | AAA | TAC | CGA | GTT | GAT | TTT | CAT | AAC | TTC | 1181 |
| Val | Ser | Lys<br>330 | Thr | Lys | Glu | Gly | Lys<br>335 | Tyr | Arg | Val | Asp<br>340 | Phe | His | Asn | Phe | |
| GGT | AAG | ACA | GTG | GAA | GTG | GAG | ACC | CCT | CAC | TGT | GCC | ATG | TGC | CTC | TAT | 1229 |
| Gly<br>345 | Lys | Thr | Val | Glu | Val<br>350 | Glu | Thr | Pro | His | Cys<br>355 | Ala | Met | Cys | Leu | Tyr<br>360 | |
| AAT | GAG | AAA | GAT | GCC | AGG | GCC | AGG | ATG | AAG | AGA | GGC | TAT | GAC | AAC | CCT | 1277 |
| Asn | Glu | Lys | Asp | Ala<br>365 | Arg | Ala | Arg | Met | Lys<br>370 | Arg | Gly | Tyr | Asp | Asn<br>375 | Pro | |
| AAC | TTT | GTC | TTG | TCA | GAA | GTT | GAT | GAA | ACG | GAC | GAC | ACC | CAG | ATG | | 1322 |
| Asn | Phe | Val | Leu<br>380 | Ser | Glu | Val | Asp | Glu<br>385 | Thr | Asp | Asp | Thr | Gln | Met<br>390 | | |

```
TAGCAGTGGC TTTTCCACCT ACAAAAAGCC TCCCAAGGAC CTAAGGGTTG ACTGTGTTCA      1382

GAAGCATCTG ACGGGGGTCT GAAAGCAGGA TGAGAACATG CGAAATCTGC TAGCACAGTC      1442

ACCCCTGAAC CCCAGGGCTA TGGTTCTACA AGACACATAG CTCTATAAGG CTGCATACGG      1502

TGCATGCATG TGAATGAAAC TGTGGAAGCC AAAGGGGCCC ACTTGGATCC TCACTATGAC      1562

TGTGTAAGCT CATATCGTGT TGATGGAAAC AAAGTCATTC AAGGACAAAA CTTAGGAGCT      1622

TTAGAAAGCT TCAGGAACTA GCCACATTTC CTGTTTGATT CTATGGATGA GAAAGATGCC      1682

ATTTTTATCT TAAAGTAGAC TTCTATCAAT GGAAAATCTG CCCTCTGCGC TGGGAAGTGA      1742

GCCAGCCAAT CAGTGACAAT AAGAGACTGT CATACAAAGA ATCAGTAAAG ACTCTAACCT      1802

TCTCAAGCTC TGGTGTTTGA AGCCTTTGTC TGAGTCTGGG TCCATGCTTC AGAAGGGGTA      1862

AGGTGACATC CACTGACTGT ACCTCTCTGA ACCCAAGGTA CAGAAGAACA GGAAGCCCCA      1922

ATCAACTTCA TAATCAACCC AGATGCTGCA GCCCATACAG AATTTGGCCT GAATGATTTC      1982

CTGTGGAGCA TTAAATGGAG GCCAAGTCCA CTCTTTAGAT ATTAAATGAA TATTCTTTTG      2042

CAAAGGAAAA AAAAAAAAA  AAAAAAA                                          2069
```

( 2 ) INFORMATION FOR SEQ ID NO:2:

( i ) SEQUENCE CHARACTERISTICS:
           ( A ) LENGTH: 391 amino acids
           ( B ) TYPE: amino acid
           ( D ) TOPOLOGY: linear ( i i ) MOLECULE TYPE: protein ( x i ) SEQUENCE DESCRIPTION: SEQ ID NO:2:

```
Met Gly Ala Ser Glu Arg Ser Val Phe Arg Val Leu Ile Arg Ala Leu
 1               5                  10                  15

Thr Glu Arg Met Phe Lys His Leu Arg Arg Trp Phe Ile Thr His Ile
                20                  25                  30

Phe Gly Arg Ser Arg Gln Arg Ala Arg Leu Val Ser Lys Glu Gly Arg
            35                  40                  45

Cys Asn Ile Glu Phe Gly Asn Val Asp Ala Gln Ser Arg Phe Ile Phe
        50                  55                  60

Phe Val Asp Ile Trp Thr Thr Val Leu Asp Leu Lys Trp Arg Tyr Lys
 65                  70                  75                  80

Met Thr Val Phe Ile Thr Ala Phe Leu Gly Ser Trp Phe Leu Phe Gly
                85                  90                  95

Leu Leu Trp Tyr Val Val Ala Tyr Val His Lys Asp Leu Pro Glu Phe
            100                 105                 110

Tyr Pro Pro Asp Asn Arg Thr Pro Cys Val Glu Asn Ile Asn Gly Met
        115                 120                 125

Thr Ser Ala Phe Leu Phe Ser Leu Glu Thr Gln Val Thr Ile Gly Tyr
    130                 135                 140

Gly Phe Arg Phe Val Thr Glu Gln Cys Ala Thr Ala Ile Phe Leu Leu
145                 150                 155                 160

Ile Phe Gln Ser Ile Leu Gly Val Ile Ile Asn Ser Phe Met Cys Gly
                165                 170                 175

Ala Ile Leu Ala Lys Ile Ser Arg Pro Lys Lys Arg Ala Lys Thr Ile
            180                 185                 190

Thr Phe Ser Lys Asn Ala Val Ile Ser Lys Arg Gly Gly Lys Leu Cys
        195                 200                 205

Leu Leu Ile Arg Val Ala Asn Leu Arg Lys Ser Leu Leu Ile Gly Ser
    210                 215                 220

His Ile Tyr Gly Lys Leu Leu Lys Thr Thr Ile Thr Pro Glu Gly Glu
225                 230                 235                 240

Thr Ile Ile Leu Asp Gln Thr Asn Ile Asn Phe Val Val Asp Ala Gly
                245                 250                 255

Asn Glu Asn Leu Phe Phe Ile Ser Pro Leu Thr Ile Tyr His Ile Ile
            260                 265                 270

Asp His Asn Ser Pro Phe Phe His Met Ala Ala Glu Thr Leu Ser Gln
        275                 280                 285

Gln Asp Phe Glu Leu Val Val Phe Leu Asp Gly Thr Val Glu Ser Thr
    290                 295                 300

Ser Ala Thr Cys Gln Val Arg Thr Ser Tyr Val Pro Glu Glu Val Leu
305                 310                 315                 320

Trp Gly Tyr Arg Phe Val Pro Ile Val Ser Lys Thr Lys Glu Gly Lys
                325                 330                 335

Tyr Arg Val Asp Phe His Asn Phe Gly Lys Thr Val Glu Val Glu Thr
            340                 345                 350

Pro His Cys Ala Met Cys Leu Tyr Asn Glu Lys Asp Ala Arg Ala Arg
        355                 360                 365

Met Lys Arg Gly Tyr Asp Asn Pro Asn Phe Val Leu Ser Glu Val Asp
    370                 375                 380

Glu Thr Asp Asp Thr Gln Met
385                 390
```

( 2 ) INFORMATION FOR SEQ ID NO:3:

( i ) SEQUENCE CHARACTERISTICS:

(A) LENGTH: 25 amino acids
(B) TYPE: amino acid
(D) TOPOLOGY: linear (ii) MOLECULE TYPE: peptide (xi) SEQUENCE DESCRIPTION: SEQ ID NO:3:

| Asp | Ala | Phe | Trp | Trp | Ala | Val | Val | Thr | Met | Thr | Thr | Val | Gly | Tyr | Gly |
|---|---|---|---|---|---|---|---|---|---|---|---|---|---|---|---|
| 1 | | | | 5 | | | | | 10 | | | | | 15 | |

| Asp | Met | Thr | Pro | Val | Gly | Phe | Trp | Gly |
|---|---|---|---|---|---|---|---|---|
| | | | 20 | | | | 25 | |

(2) INFORMATION FOR SEQ ID NO:4:

(i) SEQUENCE CHARACTERISTICS:
(A) LENGTH: 25 amino acids
(B) TYPE: amino acid
(D) TOPOLOGY: linear (ii) MOLECULE TYPE: peptide (xi) SEQUENCE DESCRIPTION: SEQ ID NO:4:

| Asp | Ala | Phe | Trp | Trp | Ala | Val | Val | Thr | Met | Thr | Thr | Val | Gly | Tyr | Gly |
|---|---|---|---|---|---|---|---|---|---|---|---|---|---|---|---|
| 1 | | | | 5 | | | | | 10 | | | | | 15 | |

| Asp | Met | Lys | Pro | Ile | Thr | Val | Gly | Gly |
|---|---|---|---|---|---|---|---|---|
| | | | 20 | | | | 25 | |

(2) INFORMATION FOR SEQ ID NO:5:

(i) SEQUENCE CHARACTERISTICS:
(A) LENGTH: 25 amino acids
(B) TYPE: amino acid
(D) TOPOLOGY: linear (ii) MOLECULE TYPE: peptide (xi) SEQUENCE DESCRIPTION: SEQ ID NO:5:

| Ala | Ala | Phe | Trp | Tyr | Thr | Ile | Val | Thr | Met | Thr | Thr | Leu | Gly | Tyr | Gly |
|---|---|---|---|---|---|---|---|---|---|---|---|---|---|---|---|
| 1 | | | | 5 | | | | | 10 | | | | | 15 | |

| Asp | Met | Val | Pro | Glu | Thr | Ile | Ala | Gly |
|---|---|---|---|---|---|---|---|---|
| | | | 20 | | | | 25 | |

(2) INFORMATION FOR SEQ ID NO:6:

(i) SEQUENCE CHARACTERISTICS:
(A) LENGTH: 25 amino acids
(B) TYPE: amino acid
(D) TOPOLOGY: linear (ii) MOLECULE TYPE: peptide (xi) SEQUENCE DESCRIPTION: SEQ ID NO:6:

| Ala | Ala | Phe | Trp | Tyr | Thr | Ile | Val | Thr | Met | Thr | Thr | Leu | Gly | Tyr | Gly |
|---|---|---|---|---|---|---|---|---|---|---|---|---|---|---|---|
| 1 | | | | 5 | | | | | 10 | | | | | 15 | |

| Asp | Met | Val | Pro | Ser | Thr | Ile | Ala | Gly |
|---|---|---|---|---|---|---|---|---|
| | | | 20 | | | | 25 | |

(2) INFORMATION FOR SEQ ID NO:7:

(i) SEQUENCE CHARACTERISTICS:
(A) LENGTH: 25 amino acids
(B) TYPE: amino acid
(D) TOPOLOGY: linear (ii) MOLECULE TYPE: peptide (xi) SEQUENCE DESCRIPTION: SEQ ID NO:7:

| Glu | Ala | Phe | Trp | Trp | Ala | Gly | Ile | Thr | Met | Thr | Thr | Val | Gly | Tyr | Gly |
|---|---|---|---|---|---|---|---|---|---|---|---|---|---|---|---|
| 1 | | | | 5 | | | | | 10 | | | | | 15 | |

```
        Asp Ile Cys Pro Thr Thr Ala Leu Gly
                 20                  25
```

( 2 ) INFORMATION FOR SEQ ID NO:8:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

```
Ala Ser Phe Trp Trp Ala Thr Ile Thr Met Thr Thr Val Gly Tyr Gly
1               5                   10                      15

Asp Ile Tyr Pro Lys Thr Leu Leu Gly
         20                  25
```

( 2 ) INFORMATION FOR SEQ ID NO:9:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

```
Ile Gly Leu Trp Trp Ala Leu Val Thr Met Thr Thr Val Gly Tyr Gly
1               5                   10                      15

Asp Met Ala Pro Lys Thr Tyr Ile Gly
         20                  25
```

( 2 ) INFORMATION FOR SEQ ID NO:10:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:10:

```
Ile Gly Phe Trp Trp Ala Val Val Thr Met Thr Thr Leu Gly Tyr Gly
1               5                   10                      15

Asp Met Tyr Pro Gln Thr Trp Ser Gly
         20                  25
```

( 2 ) INFORMATION FOR SEQ ID NO:11:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:11:

```
Thr Ala Leu Tyr Phe Thr Met Thr Cys Met Thr Ser Val Gly Phe Gly
1               5                   10                      15

Asn Val Ala Ala Glu Thr Asp Asn Glu
         20                  25
```

( 2 ) INFORMATION FOR SEQ ID NO:12:

( i ) SEQUENCE CHARACTERISTICS:
        ( A ) LENGTH: 25 amino acids
        ( B ) TYPE: amino acid (D) TOPOLOGY: linear (ii) MOLECULE TYPE: peptide (xi) SEQUENCE DESCRIPTION: SEQ ID NO:12:

Thr Cys Val Tyr Phe Leu Ile Val Thr Met Ser Thr Val Gly Tyr Gly
1               5                   10                  15

Asp Val Tyr Cys Glu Thr Val Leu Gly
            20                  25

(2) INFORMATION FOR SEQ ID NO:13:

(i) SEQUENCE CHARACTERISTICS:
    (A) LENGTH: 25 amino acids
    (B) TYPE: amino acid
    (D) TOPOLOGY: linear (ii) MOLECULE TYPE: peptide (xi) SEQUENCE DESCRIPTION: SEQ ID NO:13:

Ser Ala Phe Leu Phe Ser Leu Glu Thr Gln Val Thr Ile Gly Tyr Gly
1               5                   10                  15

Phe Arg Phe Val Thr Glu Gln Cys Ala
            20                  25

(2) INFORMATION FOR SEQ ID NO:14:

(i) SEQUENCE CHARACTERISTICS:
    (A) LENGTH: 24 amino acids
    (B) TYPE: amino acid
    (D) TOPOLOGY: linear (ii) MOLECULE TYPE: peptide (xi) SEQUENCE DESCRIPTION: SEQ ID NO:14:

Tyr Pro Glu Ile Arg Leu Asn Arg Leu Leu Arg Ile Ser Arg Met Phe
1               5                   10                  15

Glu Phe Phe Gln Arg Thr Glu Thr
            20

(2) INFORMATION FOR SEQ ID NO:15:

(i) SEQUENCE CHARACTERISTICS:
    (A) LENGTH: 24 amino acids
    (B) TYPE: amino acid
    (D) TOPOLOGY: linear (ii) MOLECULE TYPE: peptide (xi) SEQUENCE DESCRIPTION: SEQ ID NO:15:

Pro Thr Leu Phe Arg Val Ile Arg Leu Ala Arg Ile Gly Arg Ile Leu
1               5                   10                  15

Arg Leu Ile Lys Gly Ala Lys Gly
            20

(2) INFORMATION FOR SEQ ID NO:16:

(i) SEQUENCE CHARACTERISTICS:
    (A) LENGTH: 25 amino acids
    (B) TYPE: amino acid
    (D) TOPOLOGY: linear (ii) MOLECULE TYPE: peptide (xi) SEQUENCE DESCRIPTION: SEQ ID NO:16:

Asp Ala Gln Ser Arg Phe Ile Phe Phe Val Asp Ile Trp Thr Thr Val
1               5                   10                  15

Leu Asp Leu Lys Trp Arg Tyr Lys Met (2) INFORMATION FOR SEQ ID NO:17:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (xi) SEQUENCE DESCRIPTION: SEQ ID NO:17:

```
Leu Ala Ile Leu Arg Val Ile Arg Leu Val Arg Val Phe Arg Ile Phe
 1               5                  10                  15

Lys Leu Ser Arg His Ser Lys Gly
             20
```

(2) INFORMATION FOR SEQ ID NO:18:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO:18:

```
Asp Gln Phe Gln Asp Val Arg Arg Val Val Gln Val Phe Arg Ile Met
 1               5                  10                  15

Arg Ile Leu Arg Val Leu Lys Leu Ala Arg His Ser Thr Gly
             20                  25                  30
```

(2) INFORMATION FOR SEQ ID NO:19:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (xi) SEQUENCE DESCRIPTION: SEQ ID NO:19:

```
Leu Glu Asn Ala Asp Ile Leu Glu Phe Phe Ser Ile Ile Arg Ile Met
 1               5                  10                  15

Arg Leu Phe Lys Leu Thr Arg His Ser Ser Gly
             20                  25
```

PRIMARY STRUCTURE FOR FUNCTIONAL EXPRESSION FROM COMPLEMENTARY DNA OF A MAMMALIAN ATP-SENSITIVE POTASSIUM CHANNEL

FIELD OF THE INVENTION

This invention relates to the cloning of a member of a previously uncloned family of potassium channels $K_{ATP}$ channel). Specifically, the present invention discloses the cloning of ROMK1 from rat kidney outer medulla cells. Based on this disclosure, the present invention provides: 1) isolated ROMK1 cDNA sequence; 2) isolated ROMK1 protein; 3) agents capable of binding to the ROMK1 protein; and 4) methods for a) identifying other members of this potassium channel family, b) identifying agents capable of binding to members of this family, c) modulating the expression of ROMK1, d) modulating the activity of ROMK1, and e) identifying and/or testing for drugs which function as $K_{ATP}$ channel openers and $K_{ATP}$ channel closers.

BRIEF DESCRIPTION OF THE BACKGROUND ART

ATP-sensitive K+ channels ($K_{ATP}$) comprise a distinct family of potassium channels based on their biophysical, functional, and pharmacological characteristics. Five classes of $K_{ATP}$ channels are recognized based in part on differences in single channel conductance, ATP-sensitivity, pharmacology, and ion selectivity. Major properties exhibited by $K_{ATP}$ channels, best exemplified by the extensively characterized Type 1 channels from pancreatic beta-cells, include: reversible inhibition by intracellular ATP; rapid loss of channel activity in membrane patches following excision (channel rundown); MgATP-dependent maintenance of channel activity or reactivation following rundown in excised patches; inward rectification; and limited voltage-dependence in contrast to voltage-gated ion channels (Ashcroft et al., *Cellular Signalling* 2:197 (1990); Ashcroft, F. M., *Ann. Rev. Neurosci.* 11:97 (1988)).

Since the initial description of $K_{ATP}$ channels in 1983 by Noma in cardiac muscle (Noma, A., *Nature* 305:147 (1983)), there has been tremendous interest in the role of these metabolically-regulated channels in diverse physiological and pathophysiological processes involving a wide variety of both excitable (pancreatic β-cells, central neurons, cardiac, skeletal and smooth muscle cells) and non-excitable cells (renal tubular and respiratory epithelial cells) (Ashcroft et al., *Cellular Signalling* 2:197 (1990); Ashcroft, F. M., *Ann. Rev. Neurosci.* 11:97 (1988); Lang et al., *Physiol. Rev.* 72:1 (1992); Kunelmann et al., *Pflugers Arch.* 414:297 (1989)). In part, this attention has resulted from the demonstration that sulfonylureas (e.g., tolbutamide, glibenclamide) specifically inhibit and that potassium channel openers (PCOs, e.g., diazoxide, cromakalim, pinacidil, nicroandil) activate these channels in a tissue-specific manner (de Weille et al., *Pfluger Arch.* 414:S80 (1989); Sanguinetti, M. C., *Hypertension* 19:228 (1992)). Inhibition of $K_{ATP}$ channels by glucose metabolism or by sulfonylureas results in cellular depolarization and the release of insulin from pancreatic β-cells (Ashcroft et al., *Biochem. Soc. Trans.* 18:109 (1990)) and γ-aminobutyric acid (GABA) from substantia nigra cells, the latter being involved in seizure control (Amoroso et al., *Science* 247:852 (1990)). These channels also appear to be involved in ischemia-induced alterations in cardiac myocyte electrical activity and in the regulation of smooth muscle tone. Channel activation by hypoxia, metabolic insult, or PCOs is thought to result in action potential shortening together with both antiarrhythmic and proarrhythmic effects in cardiac muscle (Nichols et al., *Am. J. Physiol.* 261:H1675 (1991)) and in vascular smooth muscle relaxation (Amoroso et al., *Science* 247:852 (1990)).

The successful molecular characterization of voltage-gated ion channels (K+, Na+ and Ca2+) (Perney et al., *Curr. Opin. Cell Biol.* 3:663 (1991); Stuihmer, W., *Annu. Rev. Biophys. Chem.* 20:65 (1991); Miller, R. J., *J. Biol. Chem.* 267:1403 (1992)), cyclic nucleotide-activated channels (Kaupp et al., *Nature* 342:762 (1989); Dhallan et al., *Nature* 347:184 (1990)) and more recently of a Ca2+-activated K+ channel component (Atkinson et al., *Science* 253:551 (1991)) has greatly advanced our understanding of ion channel structure-function relationships and regulation and has revealed both common and distinctive features of each ion channel family. Voltage-gated Na+ and Ca2+ channel proteins contain four internal homologous domains with each domain consisting of six transmembrane segments and a pore-forming H5 region, while K+ channels are a tetrameric complex of polypeptides, each containing only one of these domains. To date, all K+ channels that have been cloned belong to either the superfamily of voltage-gated and second messenger-gated channels (Jan et al., *Cell* 69:715 (1992)) or to a class of channels composed of proteins with only a single membrane-spanning segment (Takumi et al., *Science* 242:1042 (1988)). The isolation of a $K_{ATP}$ channel protein or a cDNA clone, however, has remained elusive. Screening of cDNA libraries by Shaker sequence-derived oligonucleotide probes has resulted in the discovery of new members of the Shaker K+ channel family, but not in the identification of a $K_{ATP}$ channel. Moreover, approaches based on the affinity labelling of proteins from brain and a β-cell line using sulfonylurea analog have not yielded functional channel proteins (Bernardi et al., *Proc. Natl. Acad. Sci. USA* 85:981 6 (1988); Aguilar-Bryan et al., *J. Biol. Chem.* 265:8218 (1990)). Thus given the unavailability of structural information, it has not been possible to directly address issues regarding $K_{ATP}$ channel gating and regulation by ATP, phosphorylation, and G protein interactions, the types and number of channel regulatory sites, the nature of the $K_{ATP}$ channel ion-conducting pore, and the mechanisms of action of pharmaceutical agents.

SUMMARY OF THE INVENTION

The present invention is based on the cloning of a member of a previously uncloned family of potassium channels. Specifically, the present invention discloses the cloning, cDNA sequence, and amino acid sequence of ROMK1, a $K_{ATP}$ channel isolated from rat kidney outer medulla cells.

Based on this disclosure, the present invention provides isolated ROMK1 cDNA, vectors containing ROMK1, vectors capable of expressing ROMK1, and hosts transformed with vectors capable of expressing ROMK1.

The invention further provides methods of obtaining other members of this novel family of potassium channel proteins, hereinafter the ROMK1 family of channel proteins. Specifically, by using the sequence disclosed herein as a probe or as primers, and techniques such as PCR cloning and colony/plaque hybridization, one skilled in the art can obtain other members of this unique family of channel proteins.

The invention further provides isolated ROMK1 protein. Such a protein can be purified from natural sources or from cells which are engineered to express ROMK1 using standard purification techniques such as immunoaffinity chromatography.

In yet another embodiment, the invention provides for the identification, separation, purification and cloning of the genes which encode polypeptides which are associated with the ROMK1 family of channel proteins (hereinafter ROMK1 associated polypeptides).

Using the purified ROMK1 protein, the present invention provides methods of obtaining and identifying agents capable of binding to ROMK1. Specifically, such agents include antibodies, peptides, carbohydrates and pharmaceutical agents. The invention further provide detectably labeled, immobilized and toxin-conjugated forms of these agents.

The present invention further provides DNA constructs which transcribe a message which is capable of hybridizing to the message encoding ROMK1. In members of the ROMK1 family of channel proteins, such constructs are generated by placing the ROMK1 sequence in an expression vector which contains a promoter capable of transcribing the antisense strand of the ROMK1 sequence. Using such a construct, the present invention provides methods of modulating the expression of ROMK1.

The present invention further provides methods of modulating the activity of ROMK1 in a cell. Specifically, agents which are capable of binding to ROMK1 are provided to a cell expressing ROMK1. The binding of such an agent to ROMK1 can be used either to activate or inhibit the activity of ROMK1.

In addition, the present invention provides methods for identifying ROMK1-associated polypeptides that are involved in regulating or modulating ROMK1 function.

The present invention further provides methods of selectively killing cells expressing ROMK1. Specifically, a cell expressing ROMK1 can be selectively killed by providing to the cell an agent capable of binding ROMK1 which is conjugated to a cytotoxin.

The invention further provides for screening technology for the identification and/or testing of drugs for their ability to function as $K_{ATP}$ channel openers and $K_{ATP}$ channel closers.

Figure 1A:
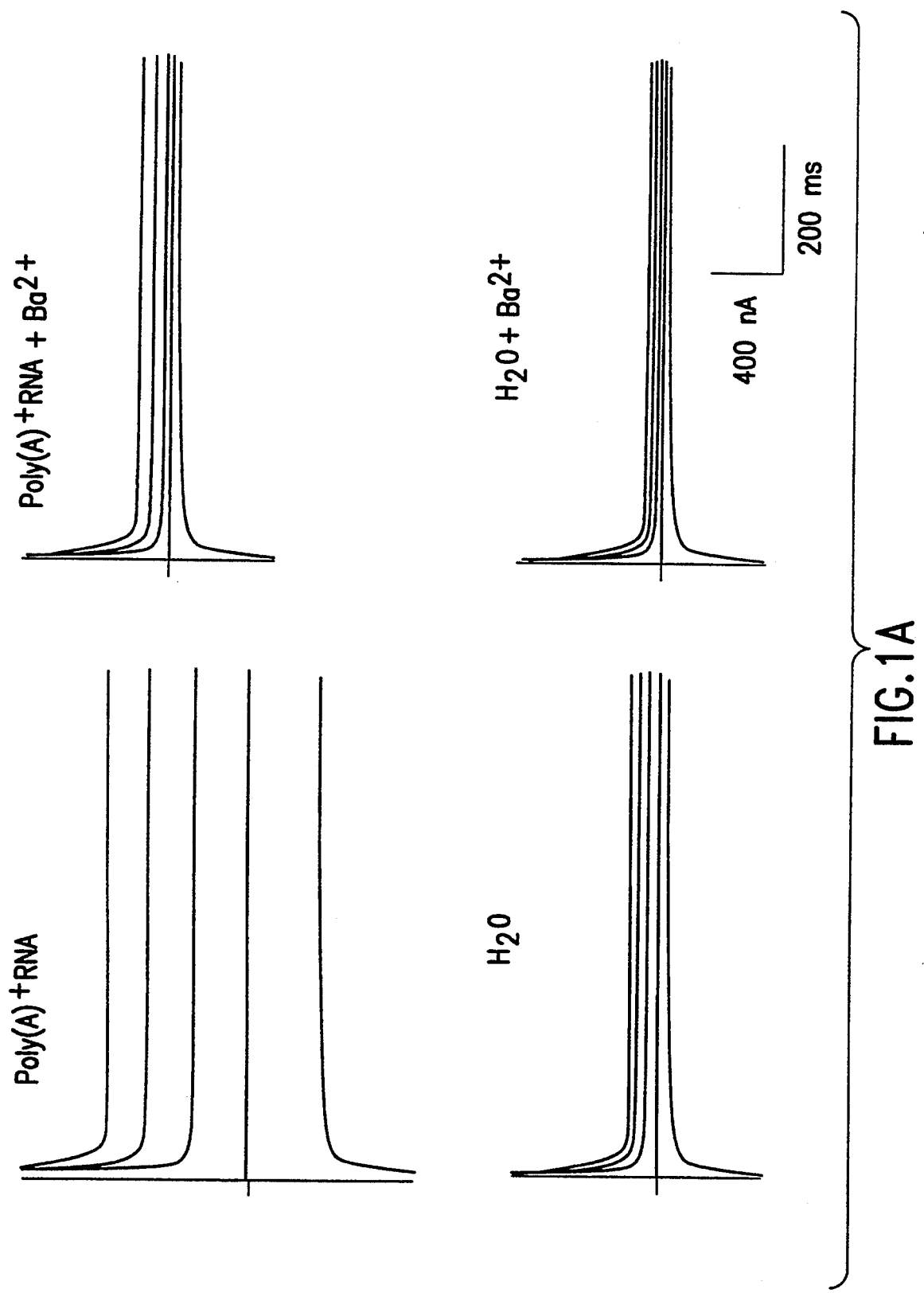
FIG. 1. $Ba^{2+}$-sensitive potassium currents ($I_{K(Ba)}$) expressed in Xenopus oocytes injected with rat kidney ISOM (inner stripe of outer medulla) poly(A)+RNA or mRNA transcribed in vitro from ROMK1 cDNA.
Figure 1B:
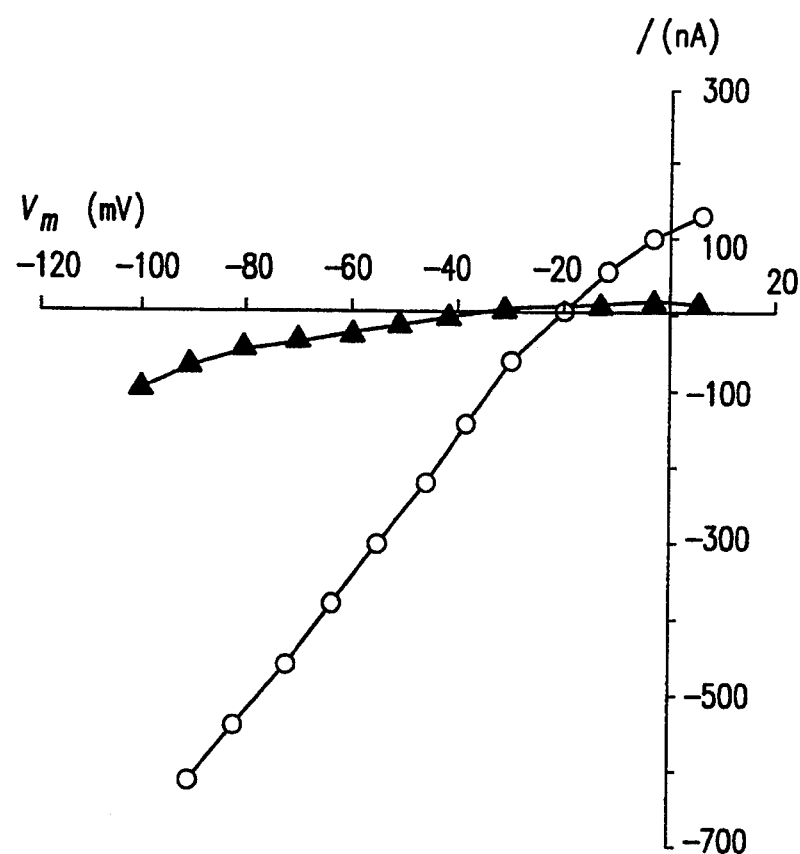
Figure 1C:
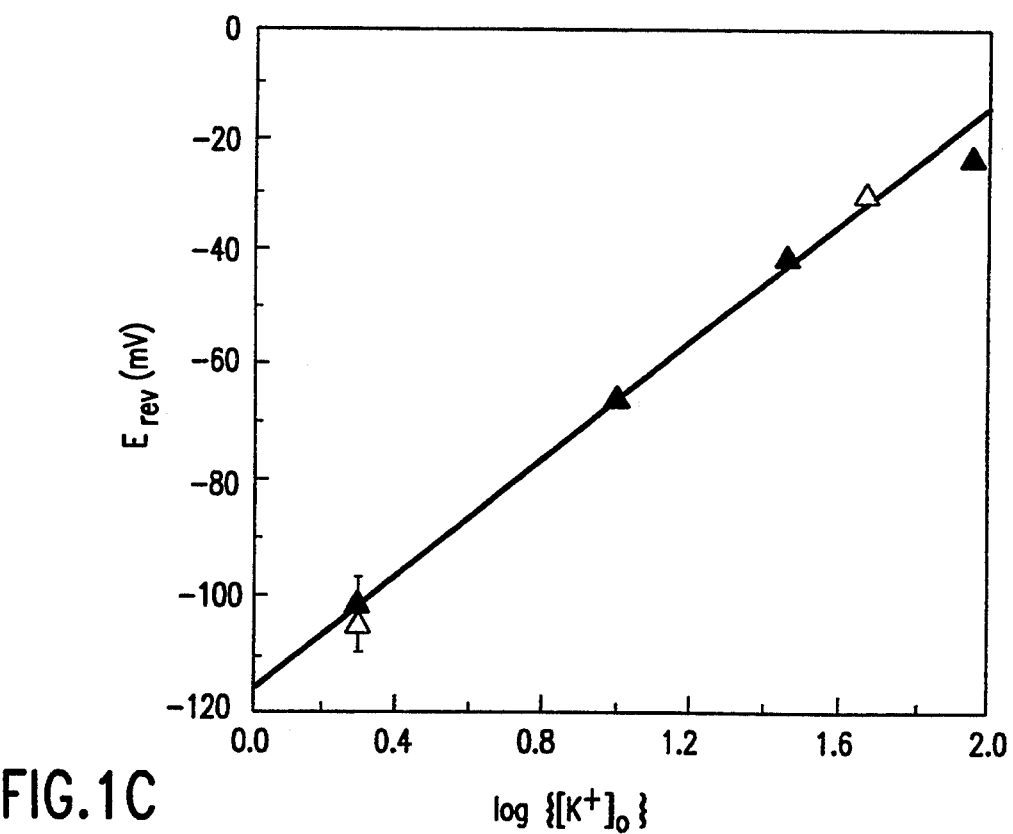
Figure 1D:
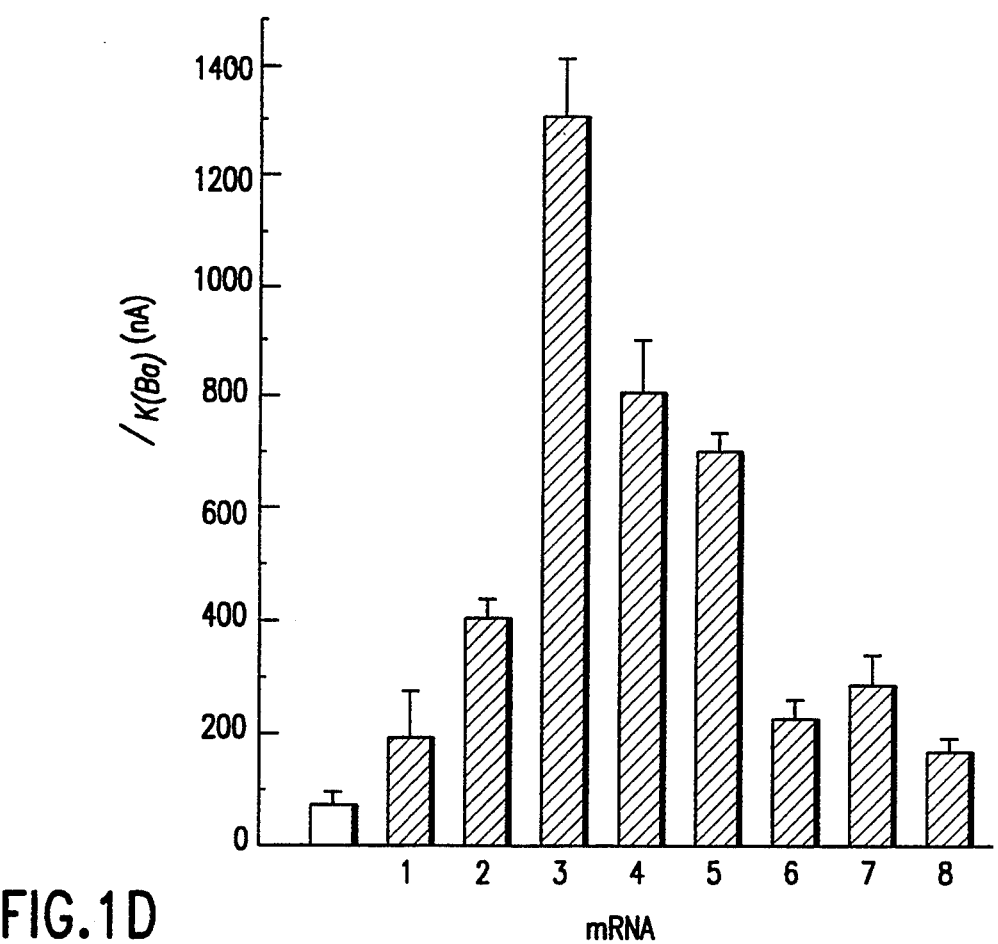
Figure 1F:
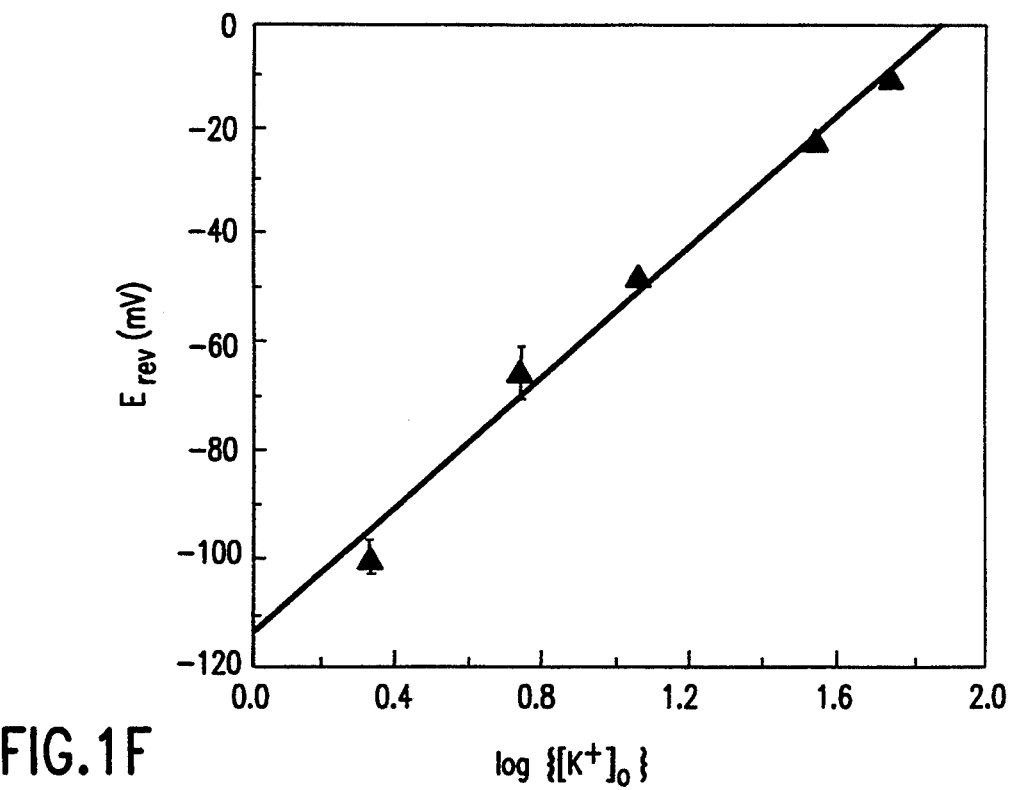
Figure 1E:
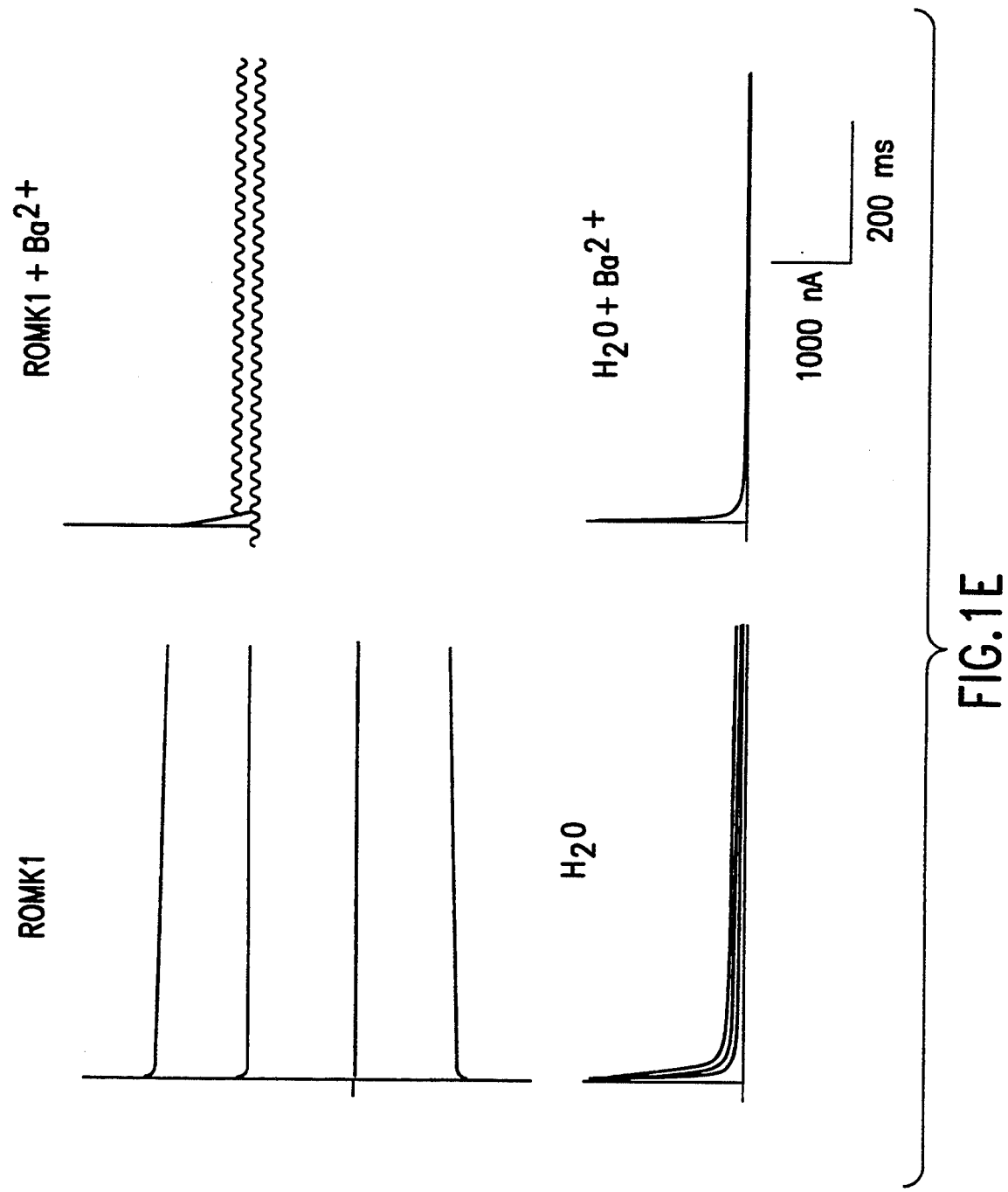

(A) Representative current tracings evoked by 450 ms voltage steps ranging from $-80$ mV to 0 mV in 20 mV increments from a holding potential ($V_H$) of $-60$ mV in oocytes injected with $\sim$25 ng ISOM poly(A)+RNA or 50 nl $H_2O$ [$K^+$]$_{ext}$=50 mM. Addition of 5 mM $Ba^{2+}$ resulted in marked inhibition of currents expressed in RNA-injected oocytes to the level of background currents in $H_2O$-injected controls over the range of test potentials used.

(B) Current-voltage relationships of $I_{K(Ba)}$ in a representative ISOM poly(A)+RNA-injected oocyte ( ) and a $H_2O$-injected control (). RNA-injected oocytes exhibited a mean $I_{K(Ba)} = -335 \pm 19$ nA, n=3] in comparison to $H_2O$-injected controls with a mean $I_{K(Ba)} = -86 \pm 8$ nA, n=28 ($V_m = -75$ mV, [$K_+$]$_{ext}$32 50 mM). Both current amplitudes and $V_m$ were measured 75 ms after initiation of test pulses; $Ba^{2+}$-sensitive current ($K_{K(Ba)}$) amplitudes were obtained by determining the difference in current amplitudes before and after the addition of 5 mM $Ba^{2+}$ at each test potential and plotted as a function of observed $V_m$.

(C) External $K^+$-dependence of reversal potentials for $I_{K(Ba)}$ in poly(A)+RNA-injected oocytes. [$K^+$]$_{ext}$ was varied by replacement with NMDG+( , n=7, (mM) 2KCl, 96 NMDG+, 10 KCl, 88 NMDG+, 30 KCl, 68 NMDG+, 90 KCl, 8 NMDG+) or with Na+(, n=4, (mM) 2 KCl, 96 NaCl, 50 KCl, 48 NaCl) in perfusion solutions containing 0.3 $CaCl_2$, 1 $MgCl_2$, 5 HEPES, pH 7.6. Points represent mean values for $E_{rev}$ (error bars, SEM) obtained from the number of oocytes indicated. $E_{rev}$ varied linearly with log [$K^+$]$_{ext}$, a linear regression line fitted to the data shows a slope of 50 mV per tenfold change in external $K^+$.

(D) $I_{K(Ba)}$ expressed in Xenopus oocytes injected with pools (#1–8) of size-fractionated ISOM poly(A)+RNA ranging from $\sim$2 to 4 kb (hatched bars) compared with $H_2O$-injected controls (open bar); bars represent mean $I_{K(Ba)}$ values from 3 to 12 oocytes. Currents were evoked by 450 ms test potentials from a $V_H = -50$ mV. Oocytes injected with mRNA of $\sim$2 to 3 kb (pool #3) exhibited a mean inward $I_{K(Ba)} = -1307 \pm 120$ nA, n=4; $H_2O$-injected controls showed a $I_{K(Ba)} \rightleftharpoons -83 \pm 14$ nA, n=8 ($V_m = -75$ mV, [$K_+$]$_{ext} \rightleftharpoons 50$ mM).

(E) Representative current tracings in oocytes injected with $\sim$0.3 ng ROMK1 mRNA or $H_2O$ evoked by 450 ms test pulses from a $V_H = -45$ mV to test potentials from $-60$ mV to 0 mV in 20 mV increments in the presence or absence of 10 mM $Ba_{2+}$, [$K_+$]$_{ext}$=50 mM. ROMK1 currents were blocked by 10 mM $Ba^{2+}$ at the test potentials used. 10 mM $TEA^+$ showed no inhibition of ROMK1 currents (dam not shown).

(F) ROMK1 $1_{K(Ba)}$ currents exhibit high $K^+$ selectivity. [$K^+$]$_{ext}$ was changed by replacement with $Na^+$ in perfusion solutions containing (mM) 0.3 $CaCl_2$, 1 $MgCl_2$, 5 HEPES, pH 8.0 as follows: 2 KCl, 96 NaCl; 5 KCl, 93 NaCl; 10 KCl, 88 NaCl; 30 KCl, 68 NaCl; 50 KCl, 48 NaCl. The $E_{rev}$ of ROMK1 $I_{K(Ba)}$ currents were dependent on [$K^+$]$_{ext}$; the linear regression line has a slope of 63 mV per tenfold change in external $K^+$. Mean values and standard errors (error bars) for $E_{rev}$ represent combined data from 5 oocytes.

FIG. 2. Single channel characteristics of ATP-sensitive ROMK1 $K^+$ channels expressed in Xenopus oocytes. Channel activities were recorded in inside-out patches excised from oocyte membranes.

(A) and (B) Current tracings recorded in the presence of 150 mM KCl or 50 mM KCl in the pipette solution. Holding potentials ($V_H$) are indicated on the left side of each tracing. Horizontal bars indicate closed channel current levels. Downward deflections represent inward currents; upward deflections represent outward currents. Three active channels are present in A; only one active channel is present in B.

(C) Current-voltage relationships of currents recorded in the presence of pipette solutions containing 150 mM KCl () or 50 mM KCl ( ) clearly display inward rectification. Unitary slope conductances of inward currents were 44 pS and 32 pS for 150 mM KCl and 50 mM KCl-containing pipette solutions, respectively. The corresponding reversal potentials extrapolated from regression lines fitted to inward currents were ~0 mV (150 mM KCl) and −28 mV (50 mM KCl) indicating high K+ selectivity.

(D) A continuous recording of both channel rundown in ATP-free bath solution and channel recovery in the same excised patch following addition of bath solution containing 0.025 mM ATP. Changes made in bath solution ATP concentration are indicated above the current recording: ATP-free (solid line), 0.025 mM ATP (dashed line). Recordings were taken at $V_H = -80$ mV. Interruptions were introduced into the recording in order to display the entire current tracing. Expanded current tracings taken from the continuous recording are indicated by numbers and arrowheads.

(E) The inhibitory effect of 2.5 mM ATP on channel activity. Changes in bath solution ATP concentration are indicated above the current recording; 0.025 mM ATP (dashed line), 2.5 mM ATP (solid line). The inside-out patch was continuously perfused with bath solution containing 0.025 mM ATP; an increase in ATP concentration to 2.5 mM was achieved at the cytosolic side of the membrane patch using a puffer pipette over the time interval shown and resulted in inhibition of channel activity. Exposure of the patch to 0.025 mM ATP-containing bath solution after removal of the puffer pipette from the bath resulted in restoration of channel activity. The recording was taken at $V_H = -40$ mV. Expanded current tracings taken from the recording at various time intervals are indicated by arrows and numbers. The pipette solution contained (mM): 150 or 50 KCl, 1 CaCl$_2$, 1 MgCl$_2$, 5 HEPES (pH 7.4). The bath solution contained (mM): 0,0.025 or 2.5 MgATP, 150 KCl, 1 MgCl$_2$, 5 EGTA, 5 HEPES (pH 7.4).

FIG. 3. Nucleotide sequence of ROMK1 cDNA. Protein coding region begins with the ATG in position 210 and ends with the stop codon, TGA, in position 1323, deduced amino acid sequence is shown in three-letter code. 5' and 3' untranslated regions show nucleotides in lower case; translated region have nucleotides in upper case. Potential membrane spanning regions [M0, M 1 and M2] are underlined. The putative channel pore-forming region [H5-like] is boxed. The Walker Type A and Type B, ATP-binding sequences, are shown in bold type.

Figure 4A:
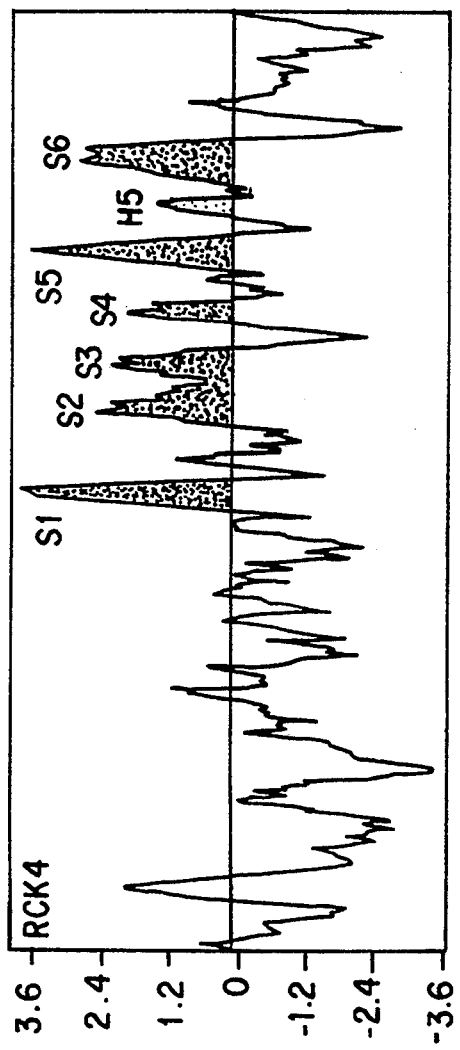
Figure 4B:
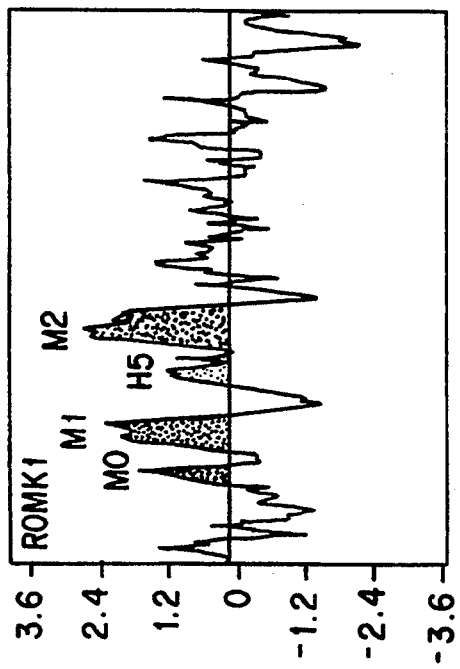
Figure 4C:
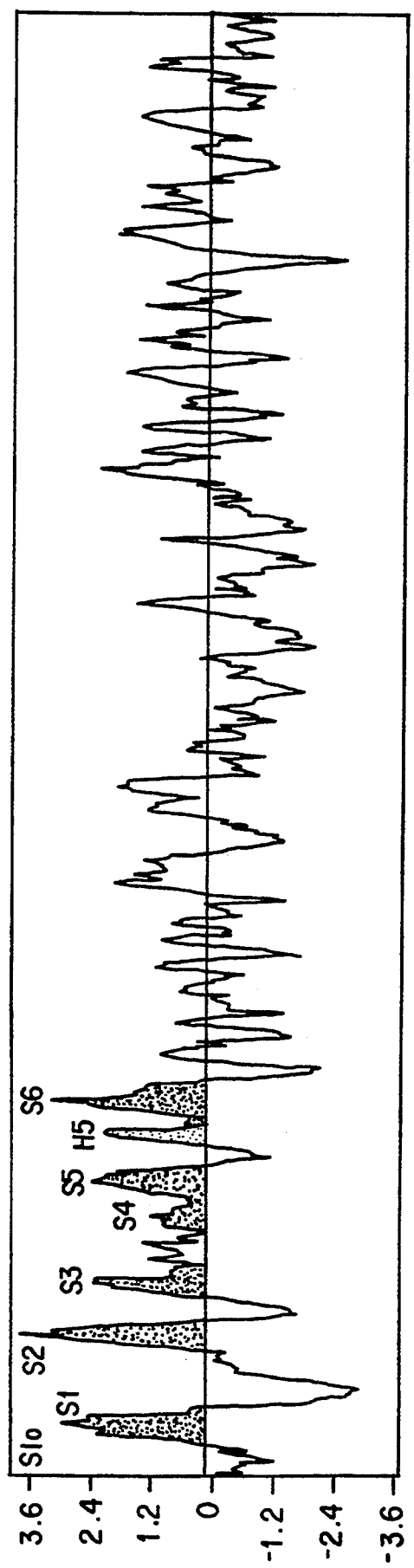

FIG. 4. Comparison of Kyte-Doolittle hydropathy histogram plots of ROMK1 [K$_{ATP}$ family] and two members of the voltage-dependent potassium channel family, RCK4 and Slo. The major hydrophilic regions are dark shaded. Note completely different topology of ROMK1 compared to the voltage-gated channels. Also note the four hydrophilic regions in ROMK1 [potential membrane spanning regions M0, M1 and M2 and the H5-like region].

FIG. 5. Homology of ROMK1 with the voltage-gated potassium channel H5 and S4 regions.

(A) H5 homology. Shaker proteins are shown above the mammalian homologue for the four classes of voltage-gated potassium channels. Eag and Slo are shown above ROMK1 at the bottom. Comparisons are made to Shaker A; identical amino acids are shaded; conservative changes are boxed.

(B) Homology of ROMK1 M0 region with the S4 regions of the voltage-gated potassium [Shaker A, Shab 11 and Shaw 2] and voltage-gated sodium (Na+ brain 1 ] channels and similar regions in the ligand-gated channels [cGMP-gated]. Regions of identity or conserved changes are boxed.

Figure 6:
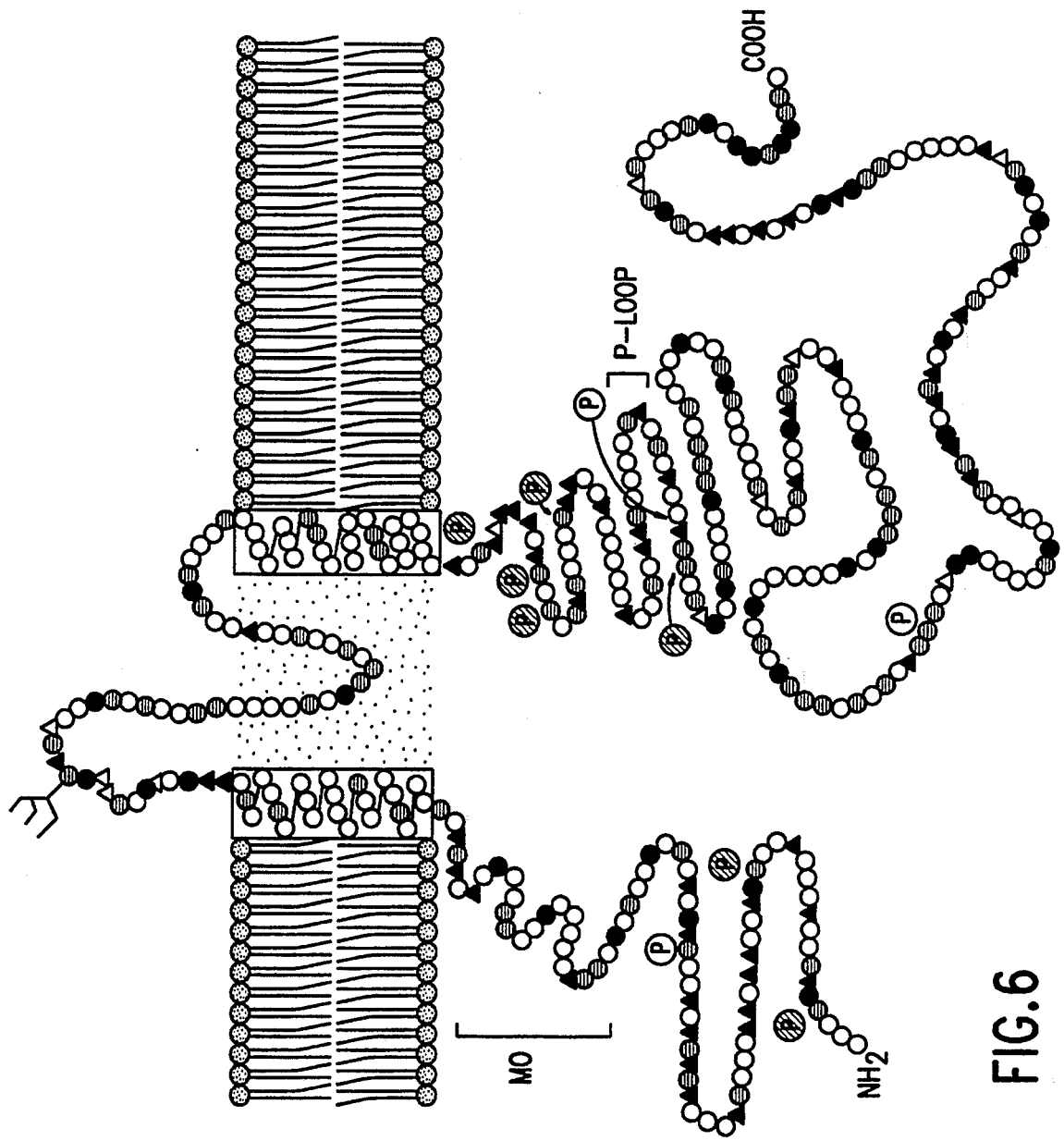

FIG. 6. Model of ROMK1 protein. Membrane spanning regions M1 and M2 are shown in the membrane together with the pore-forming region, P, and the H5-like region. A single glycosylation site is shown on the extracellular face of the protein between M 1 and the H5-like region. The ATP-binding site is indicated as the Walker type A, P-loop. The partially hydrophobic region, M0, is placed outside the membrane on the intracellular side, however, this region could be partly associated with the membrane. "P" in an open circle represented a putative cyclic AMP-dependent protein kinase phosphorylation site; "P" in a solid circle represents a putative protein kinase C phosphorylation site. [open circles—hydrophobic amino acids; striped circle—noncharged, polar amino acids; solid circles—negatively charged amino acids; solid triangles—positively charged amino acids; open triangles—proline].

Figure 7B:
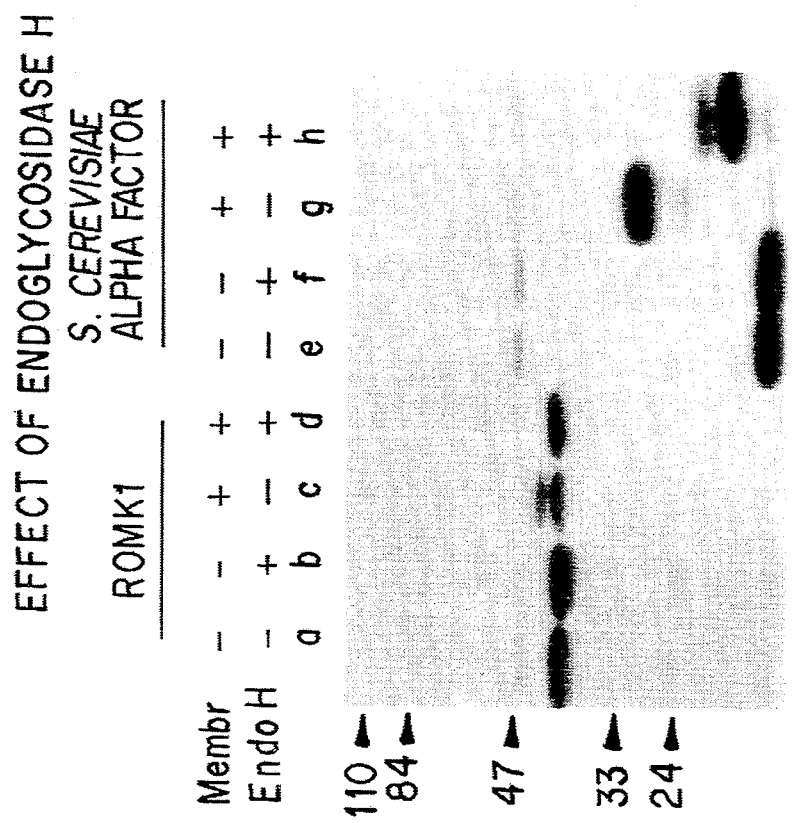
Figure 7A:
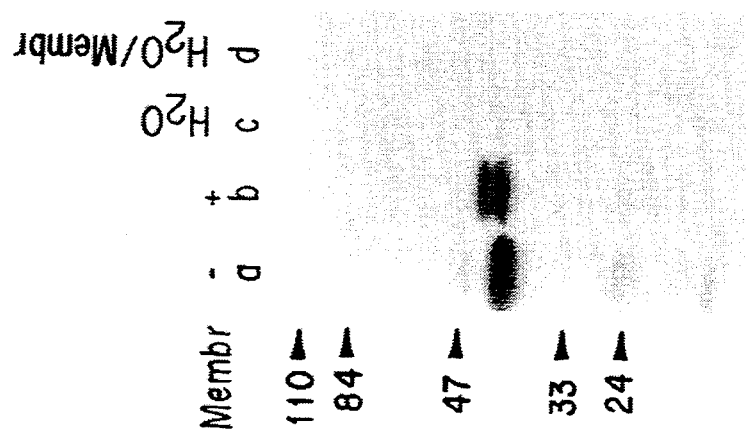

FIG. 7. In vitro translation of synthetic messenger RNA (cRNA) made from ROMK1 cDNA.

(A) Translation using rabbit reticulocyte lysate without (lane a) or with (lane b) dog pancreatic microsome membranes. Lanes c and d are water controls without and with membranes, respectively. ROMK1 translates to a 45 kDA protein that is glycoslyated in the presence of membranes.

(B) Effect of the glycosidase, Endo H, on in vitro translation of ROMK1 cRNA. Lanes a-d demonstrate that ROMK1 protein is a glycoprotein. Lanes e-f are translation-glycosylation controls.

DETAILED DESCRIPTION OF THE INVENTION

The present invention is based on the cloning of a member of a previously uncloned family of potassium channels. Specifically, the present invention discloses the cloning, cDNA sequence, and amino acid sequence of ROMK1, K$_{ATP}$ channel isolated from rat outer medulla cells.

Based on this disclosure, the present invention provides the nucleotide sequence encoding ROMK1 (Sequence ID No. 2). In detail, the present invention provides the previously unknown DNA sequence identified as Sequence ID No. 1.

The invention further provides vectors containing sequences encoding ROMK1. Such vectors included, but are not limited to, plasmid, phage, retrovirus and baculovirus vectors. One skilled in the art can readily place the sequences of the present invention into any known suitable vector using routine procedures.

The invention further includes vectors containing all of the elements necessary to express the ROMK1 sequence, or members of the ROMK1 family of channel proteins. Such elements can include, but are not limited to, promoters, ribosome binding sites, polyadenylation signals, termination signals, and capping signals. As above, one skilled in the art can readily generate such expression vectors using known methods.

The invention further provides methods of obtaining other members of this novel family (the ROMK1 family) of potassium channel.

As used herein, a potassium channel is said to be "a member of the ROMK1 family of channel protein" if it shares significant homology to one or more regions of the ROMK1 protein. Specifically, by using the sequence disclosed herein as a probe or as primers, and techniques such as PCR cloning and colony/plaque hybridization, one skilled in the art can obtain other members of the ROMK1 family of channel proteins as well as genomic sequences encoding the ROMK1 family members.

As used herein, a protein is said to "share significant homology" if the two proteins, contains regions which process greater than 50% homology.

Region specific primers or probes derived from Sequence ID No. 1 can be used to prime DNA synthesis and PCR amplification, as well as to identify colonies containing cloned DNA encoding a member of the ROMK1 family using known methods (Innis et al., *PCR Protocols*, Academic Press, San Diego, Calif. (1990)).

When using primers derived from ROMK1 for amplification, one skilled in the art will recognize that by employing high stringency condition, annealing at 50°–60° C., sequences which are greater than 75% homologous to the primer will be amplified. By employing lower stringency conditions, annealing at 35°–37° C., sequences which are greater than 40–50% homologous to the primer will be amplified.

When using DNA probes derived from ROMK1 for colony/plaque hybridization, one skilled in the art will recognize that by employing high stringency condition, hybridization at 50°–65° C. 5X SSPC, 50% formamide, wash at 50°–65° C., 0.5X SSPC, sequences having regions which are greater than 90% homologous to the probe can be obtained, and by employing lower stringency conditions, hybridization at 35°–37° C., 5X SSPC, 40–45% formamide, wash at 42° C., SSPC, sequences having regions which are greater than 35–45% homologous to the probe will be obtained.

Any tissue can be used as the source for the genomic DNA or RNA encoding members of the ROMK1 family of potassium channels. However, with respect to RNA, the most preferred source is tissues which express elevated levels of the desired potassium channel family member. In the present invention, oocyte injection and two-electrode whole oocyte clamping and patch clamping of single channels was used to identify expression from such a tissue source. However, using the sequences disclosed herein, it is now possible to identify such cells using the ROMK1 sequence as a probe in northern blot or in situ hybridization procedures, thus eliminating the necessity of the procedures employed to clone the first member of this family and eliminating the need to obtain RNA/DNA from a tissue which expresses elevated levels of ROMK1 protein.

The present invention further provides methods of identifying cells or tissues which express a member of the ROMK1 family of channel proteins. In detail, a probe comprising the DNA sequence of Sequence ID No. 1, a fragment thereof, or a DNA sequence encoding another member of the ROMK1 family of channel proteins can be used as a probe or amplification primer to detect cells which express a message homologous to the probe or primer. One skilled in the art can readily adapt currently available nucleic acid amplification or detection techniques so that it employs probes or primers based on the sequences encoding a member of the ROMK1 family.

The materials for use in the invention are ideally suited for the preparation of a kit. Specifically, the invention provides a kit compartmentalized to receive in close confinement, one or more containers which comprises: (a) a first container comprising one or more probes or amplification primers based on the ROMK1 sequence; and (b) one or more other containers comprising one or more of the following: a sample reservoir, wash reagents, reagents capable of detecting presence of bound probe from the first container, or reagents capable of amplifying sequences hybridizing to the amplification primers.

In detail, a compartmentalized kit includes any kit in which reagents are contained in separate containers. Such containers include small glass containers, plastic containers or strips of plastic or paper. Such containers allow one to efficiently transfer reagents from one compartment to another compartment such that the samples and reagents are not cross-contaminated and the agents or solutions of each container can be added in a quantitative fashion from one compartment to another. Such containers will include a container which will accept the test sample, a container which contains the probe or primers used in the assay, containers which contain wash reagents (such as phosphate buffered saline, Tris-buffers, etc.), and containers which contain the reagents used to detect the bound probe or amplified product.

Types of detection reagents include labelled secondary probes, or in the alternative, if the primary probe is labelled, the enzymatic, or antibody binding reagents which are capable of reacting with the labelled probe. One skilled in the art will readily recognize that probes and amplification primers based on the sequence disclosed in the present invention can be readily incorporated into one of the established kit formats which are well known in the art.

In one example, a first container may contain a hybridization probe. Other containers may contain reagents useful in the localization of labelled probes, such as enzyme substrates. Still other containers may contain buffers, etc.

The present invention further provides functional derivatives of the ROMK1 sequence. As used herein, the term "functional derivative" is used to define any DNA sequence which is derived from the original DNA sequence and which still possesses at least one of the biological activities present in the parent molecule. A functional derivative can be an insertion, deletion, or a substitution of one or more bases in the original DNA sequence. Functional derivatives of ROMK1 therefore include, but are not limited to derivatives which have altered ATP binding, altered potassium gating capacity, and altered cofactor requirements.

Functional derivatives of Sequence ID No. 1 having an altered nucleic acid sequence can be prepared by mutagenesis of the DNA. This can be accomplished using one of the mutagenesis procedures known in the art.

Preparation of functional derivatives of Sequence ID No. 1 are preferably achieved by site-directed mutagenesis. Site-directed mutagenesis allows the production of functional derivatives of Sequence ID No. 1 through the use of a specific oligonucleotide which contains the desired mutated DNA sequence.

Site-directed mutagenesis typically employs a phage vector that exists in both a single-stranded and double-stranded form. Typical vectors useful in site-directed mutagenesis include vectors such as the M 13 phage, as disclosed by Messing et al., *Third Cleveland Symposium on Macromolecules and Recombinant DNA*, Editor A. Walton, Elsevier, Amsterdam (1981), the disclosure of which is incorporated herein by reference. These phage are commercially available and their use is generally well known to those skilled in the art. Alternatively, plasmid vectors containing a single-stranded phage origin of replication (Veira et al., *Meth. Enzymol.* 153:3 (1987)) may be employed to obtain single-stranded DNA.

In general, site-directed mutagenesis in accordance herewith is performed by first obtaining a single-stranded vector that includes within its sequence the DNA sequence which is to be altered. An oligonucleotide primer bearing the desired mutated sequence is prepared, generally synthetically, for example by the method of Crea et al., *Proc. Natl. Acad. Sci. (USA)* 75:5765 (1978). The primer is then annealed with the single-stranded vector containing the sequence which is to be altered, and the created vector is incubated with a DNA-polymerizing enzyme such as *E. coli* polymerase I Klenow fragment in an appropriate reaction buffer. The polymerase will complete the synthesis of a mutation-bearing strand. Thus, the second strand will contain the desired mutation. This heteroduplex vector is then used to transform appropriate cells, such as JM101 cells, and clones are selected that contain recombinant vectors bearing the mutated sequence.

While the site for introducing a sequence variation is predetermined, the mutation per se need not be predetermined. For example, to optimize the performance of a mutation at a given site, random mutagenesis may be conducted at a target region and the newly generated sequences can be screened for the optimal combination of desired activity.

It is difficult to predict the exact effect of the substitution, deletion, or insertion in advance of doing so. However, one skilled in the art will recognize that the functionality of the derivative can be evaluated by routine screening assays. For example, mRNA encoded by a functional derivative made by site-directed mutagenesis can be injected into an oocyte as described in the Examples and the oocyte tested for channel activity.

Using genomic sequence corresponding to the ROMK1 family of channel proteins (the isolation of which is described above), the present invention further provides methods of directing the expression of a heterologous gene in the same temporal and spatial manner as the ROMK1 channel protein. In detail, using chromosome walking techniques and DNA sequence analysis, the regulatory elements responsible for the tissue specific expression of ROMK1 can readily be obtained by one skilled in the art. These elements, such as, but not limited to, tissue specific promoters and enhancers, can readily be operably linked to a heterologous gene such that the heterologous gene is expressed in a cell in the same temporal and spatial manner as the ROMK1 gene.

The invention further provides an isolated protein of the ROMK1 family of channel proteins. Specifically, the present invention provides a protein comprising the amino acid sequence of Sequence ID No. 2.

Any eukaryotic organism can be used as a source for a protein which is a member of the ROMK1 protein, or the genes encoding same, so long as the source organism naturally expresses such a protein or contains genes encoding same. As used herein, "source organism" refers to the original organism from which the amino acid or DNA sequence of the protein is derived, regardless of the organism the protein is expressed in and ultimately isolated from. For example, a member of the ROMK1 family of channel proteins expressed in hamster cells is of human origin as long as the amino acid sequence is that of a human protein which is a member of this family. The most preferred source organism for ROMK1 protein is rats or humans.

A variety of methodologies known in the art can be utilized to obtain a member of the ROMK1 family of channel proteins. In one method, the protein is purified from tissues or cells which naturally produce the protein. One skilled in the art can readily follow known methods for isolating proteins in order to obtain a member of the ROMK1 protein family, free of natural contaminants. These include, but are not limited to, immunochromatography, HPLC, size-exclusion chromatography, ion-exchange chromatography, and immunoaffinity chromatography.

In another embodiment, a member of the ROMK1 family of channel proteins is purified from cells which have been altered to express the desired protein.

As used herein, a cell is said to be "altered to express a desired protein" when the cell, through genetic manipulation, is made to produce a protein which it normally does not produce or which the cell normally produces at low levels. One skilled in the art can readily adapt procedures for introducing and expressing either genomic, cDNA, or synthetic sequences into either eukaryotic or prokaryotic cells in order to generate a cell which produces a member of the ROMK1 family of channel proteins.

There are a variety of sources for DNA encoding members of the ROMK1 family of channel proteins. One of these is the sequence of the ROMK1 protein depicted in Sequence ID No. 2. The DNA can be isolated as described herein from a source such as human, or, alternatively, the sequence encoding the ROMK1 family member can be synthesized utilizing the DNA sequences disclosed herein.

Any host/vector system can be used to express a member of the ROMK1 family of channel proteins. These include, but are not limited to, eukaryotic hosts such as Hela cells, Cv-1 cell, COS cells, and Sf9 cells, as well as prokaryotic host such as *E. coli* and *B. subtills*. The most preferred cells are those which do not normally express the member of the ROMK1 family of channel proteins or which expresses such a protein at low levels.

The members of the ROMK1 family of channel proteins, as well as the example of this family which is depicted in Sequence ID No. 2 can be used in a variety procedures and methods known in the art which are currently applied to other proteins.

For example, the ROMK1 family member is used to generate an antibody which is capable of binding to the channel protein.

The antibodies of the present invention include monoclonal and polyclonal antibodies, as well fragments of these antibodies, and humanized forms. Humanized forms of the antibodies of the present invention may be generated using one of the procedures known in the art such as chimerization or CDR grafting. Fragments of the antibodies of the present invention include, but are not limited to, the Fab, the Fab2, and the Fd fragment.

The invention also provides hybridomas which are capable of producing the above-described antibodies. A hybridoma is an immortalized cell line which is capable of secreting a specific monoclonal antibody.

In general, techniques for preparing polyclonal and monoclonal antibodies as well as hybridomas capable of producing the desired antibody are well known in the art (Campbell, A. M., "*Monoclonal Antibody Technology: Laboratory Techniques in Biochemistry and Molecular Biology,*" Elsevier Science Publishers, Amsterdam, The Netherlands (1984); St. Groth et al., *J. Immunol. Methods* 35:1-21 (1980)).

Any animal (mouse, rabbit, etc.) which is known to produce antibodies can be immunized with the pseudogene polypeptide. Methods for immunization are well known in the art. Such methods include subcutaneous or interperitoneal injection of the polypeptide. One skilled in the art will recognize that the amount of the ROMK1 family of channel proteins used for immunization will vary based on the animal which is immunized, the antigenicity of the peptide and the site of injection.

The protein which is used as an immunogen may be modified or administered in an adjuvant in order to increase the protein's antigenicity. Methods of increasing the antigenicity of a protein are well known in the art and include, but are not limited to coupling the antigen with a heterologous protein (such as globulin or $\beta$-galactosidase) or through the inclusion of an adjuvant during immunization.

For monoclonal antibodies, spleen cells from the immunized animals are removed, fused with myeloma cells, such as SP2/0-Ag 14 myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz et al., *Exp. Cell Res.* 175:109–124 (1988)).

Hybridomas secreting the desired antibodies are cloned and the class and subclass is determined using procedures known in the art (Campbell, A. M., *Monoclonal Antibody Technology: Laboratory Techniques in Biochemistry and Molecular Biology*, Elsevier Science Publishers, Amsterdam, The Netherlands (1984)).

For polyclonal antibodies, antibody containing antisera is isolated from the immunized animal and is screened for the presence of antibodies with the desired specificity using one of the above-described procedures.

The present invention further provides the above-described antibodies in detectably labelled form. Antibodies can be detectably labelled through the use of radioisotopes, affinity labels (such as biotin, avidin, etc.), enzymatic labels (such as horseradish peroxidase, alkaline phosphatase, etc.) fluorescent labels (such as FITC or rhodamine, etc.), paramagnetic atoms, etc. Procedures for accomplishing such labelling are well-known in the art, for example see (Sternberger, L. A. et al., *J. Histochem. Cytochem.* 18:315 (1970); Bayer, E. A. et al., *Meth. Enzym.* 62:308 (1979); Engval, E. et al., *Immunol.* 109:129 (1972); Goding, J. W. *J. Immnunol. Meth.* 13:215 (1976)).

The labeled antibodies of the present invention can be used for in vitro, in vivo, and in situ assays to identify cells or tissues which express a member of the ROMK1 family of channel proteins or to identify samples containing the protein.

The present invention further provides the above-described antibodies immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir, D. M. et al., *"Handbook of Experimental Immunology"* 4th Ed., Blackwell Scientific Publications, Oxford, England, Chapter 10 (1986); Jacoby, W. D. et al., *Meth. Enzym.* 34 Academic Press, N.Y. (1974)). The immobilized antibodies of the present invention can be used for in vitro, in vivo, and in situ assays as well as for immunoaffinity purification of the ROMK1 channel protein family member.

The present invention further provides the antibodies of the present invention conjugated to a cytotoxin. Examples of such cytotoxins include, but are not limited to, Ricin A chain, diphtheria toxin, cholera toxin, as well as radionuclides. Methods of conjugation antibodies, there use, and the types of toxins currently employed is disclosed in Golbert et at., *Cancer Diagnosis and Therapy with Radiolabeled Antibodies* pp. 259–280, Oxford Press, N.Y.(1987); Vitetta et al., *Science* 219:644 (1983), and Pastan et al., *Cell* 47:641–648 (1986).

The present invention further provides methods of identify the expression of a member of the ROMK1 family of channel proteins in a test sample.

In detail, the methods comprise incubating a test sample with one or more of the antibodies of the present invention and assaying for binding of the antibody to the test sample.

Conditions for incubating an antibody with a test sample vary. Incubation conditions depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ the antibodies of the present invention. Examples of such assays can be found in Chard, T. *"An Introduction to Radioimmunoassay and Related Techniques"* Elsevier Science Publishers, Amsterdam, The Netherlands (1986); Bullock, G. R. et al., *"Techniques in Immunocytochemistry,"* Academic Press, Orlando, Fla. Vol. 1 (1982), Vol. 2 (1983), Vol. 3 (1985); Tijssen, P., *"Practice and Theory of Enzyme Immunoassays: Laboratory Techniques in Biochemistry and Molecular Biology,"* Elsevier Science Publishers, Amsterdam, The Netherlands (1985).

The test samples of the present invention include cells, protein or membrane extracts of cells, or biological fluids such as blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the an and can be readily be adapted in order to obtain a sample which is capable with the system utilized.

In another embodiment of the present invention, kits are provided which contain the necessary reagents to carry out the previously described assays.

Specifically, the invention provides a compartmentalized kit to receive, in close confinement, one or more containers which comprises: (a) a first container comprising one of the antibodies of the present invention; and (b) one or more other containers comprising one or more of the following: wash reagents, reagents capable of detecting presence of bound antibodies.

In detail, a compartmentalized kit includes any kit in which reagents are contained in separate containers. Such containers include small glass containers, plastic containers or strips of plastic or paper. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the antibodies used in the assay, containers which contain wash reagents (such as phosphate buffered saline, Tris-buffers, etc.), and containers which contain the reagents used to detect the bound antibody.

Types of detection reagents include labelled secondary antibodies, or in the alternative, if the primary antibody is labelled, the enzymatic, or antibody binding reagents which are capable of reacting with the labelled antibody. One skilled in the art will readily recognize that the disclosed antibodies of the present invention can readily be incorporated into one of the established kit formats which are well known in the art.

The present invention further provides anti-ROMK1 anti-idiotypic antibodies. In detail, the anti-ROMK1 antibodies are suitable for use in generating anti-idiotypic antibodies.

Anti-idiotypic antibodies can be generated by any of the methods described above using one of the antibodies of the present invention as an immunogen, for example see Hellstrom et al., U.S. Pat. No. 4,918,164, or Shecter et al., *Anti-Idiotypes, Receptor, and Molecular Mimicry* p 73, D. S. Linthicum et al., eds. New York (1988). One skilled in the art can readily adapt known methods in order to generate the anti-idiotypic antibodies capable of binding to the antigen binding site of the anti-pseudogene peptide antibodies of the present invention.

Using the purified ROMK1 protein, the present invention provides methods of obtaining and identifying agents capable of binding to ROMK1. Specifically, such agents include antibodies (described above), peptides, carbohydrates, pharmaceutical agents and the like.

In detail, said method comprises:
(a) contacting an agent with a purified member of the ROMK1 family of channel proteins; and
(b) determining whether the agent binds to said protein.

The agents screened in the above assay can be, but are not limited to, peptides, carbohydrates, vitamin derivatives, or other pharmaceutical agents. The agents can be selected and screened at random or rationally selected or designed using protein modeling techniques.

For random screening, agents such as peptides, carbohydrates, pharmaceutical agents and the like are selected at random and are assayed for their ability to bind to the ROMK1 family member as outlined above.

Alternatively, agents may be rationally selected or designed. As used herein, an agent is said to be "rationally selected or designed" when the agent is chosen based on the configuration of the ROMK1 family of channel proteins. For example, one skilled in the art can readily adapt currently available procedures to generate peptides, pharmaceutical agents and the like capable of binding to a specific peptide sequence in order to generate rationally designed antipeptide peptides', for example see Hurby et al., "Application of Synthetic Peptides: Antisense Peptides", In *Synthetic Peptides, A User's Guide*, W. H. Freeman, N.Y., pp. 289–307 (1992), and Kaspczak et al., *Biochemistry* 28:9230–8 (1989), or pharmaceutical agents, or the like.

Anti-peptide peptides can be generated in one of two fashions. First, the anti-peptide peptides can be generated by replacing the basic amino acid residues found in the ROMk1 protein with acidic residues, while maintaining hydrophobic and uncharged polar groups. For example, lysine, arginine, and/or histidine residues are replaced with aspartic acid or glutamic acid and glutamic acid residues are replaced by lysine, arginine or histidine.

Alternatively, the anti-peptide peptides of the present invention can be generated by synthesizing and expressing a peptide encoded by the antisense strand of the DNA which encodes the ROMK1 family member. Peptides produced in this fashion are, in general, similar to those described above since codons complementary to those coding for basic residues generally code for acidic residues.

The cloning of ROMK1 now makes possible the screening capability which enables the identification of agonists ($K_{ATP}$ channel openers) and antagonists ($K_{ATP}$ channel closers) of the ROMK1 family of channel proteins. $K_{ATP}$ channel openers are smooth muscle relaxants, functioning as vasodilators, vasospasmolytics, and other smooth muscle spasmolytic. As vasodilators, these compounds have use as dilators of peripheral vasculature, coronary arteries, renal vasculature, cerebral vasculature, and mesenteric vasculature. As vasospasmolytics, these compounds have use in the treatment of coronary artery spasm, peripheral vascular spasm, cerebral vascular spasm and impotence. Other smooth muscle spasmolytics have use as bronchodilators, in the control of urinary bladder and gall bladder spasm, and in the control of esophageal, gastric, and intestinal smooth muscle spasm.

$K_{ATP}$ channel closers function in the pancreas to enhance release of insulin, in the kidney as diuretics and renal epithelial anti-ischemic agents, as hypertensive agents for promoting vasoconstriction for use in hypotensive states as antiarrhythmic agents, and as agents for modifying cardiac muscle contractility.

Other uses for $K_{ATP}$ channel agonists or antagonists include cardiac antiarrhythmic agents, agents effective in reducing ischemia-induced cardiac damage, agents effective in reducing ischemia-induced brain damage, anticonvulsants, hair growth promoting agents, and agents effective in preventing or reducing skeletal muscle damage or fatigue.

The invention further provides detectably labeled, immobilized and toxin conjugated forms of these agents. Such modified agents can be generated using the procedures described above for modifying antibodies.

The present invention further provides methods for modulating the activity of ROMK1, or a member of the ROMK1 family of channel proteins. Specifically, the activity of a member of the ROMK1 family of channel proteins can be modulated by providing to cells expressing such a protein an agent capable of binding to the channel protein. Such agents include, but are not limited to, the anti-ROMK1 antibodies and the antipeptide peptides of the present invention. By providing such an agent to a cell, the activity of the ROMK1 family member can either be blocked or stimulated. Such agents can be used to treat any of the physiological or pathophysiological conditions which are associated with the ROMK1 class of potassium channels, for example see Weston, A. H., *Pflugers Arch.* 414 (Suppl. 1):S99–S105 (1989), Tsuura, et al., *Diabetes* 41:861–865 (1992), and Escande, D. *Pflugers Arch.* 414 (Suppl 1):S93–S98 (1989).

The present invention further provides methods for modulating the expression of ROMK1, or a member of the ROMK1 family of channel proteins. Specifically, anti-sense RNA expression is used to disrupt the translation of the mRNA encoding the ROMK1 protein.

In detail, a cell is modified using routine procedures such that if expresses an antisense mRNA, an mRNA which is complementary to mRNA encoding the ROMK1 family member. By constitutively or inducibly expressing the antisense RNA, the translation of the ROMK1 family member mRNA can be regulated. Such antisense technology has been successfully applied to regulate the expression of poly(ADP-ribose) polymerase (Ding et al., *J. Biol. Chem.* 267:12804–12812 (1992)) as well as other proteins.

The present invention further provides methods of selectively killing cells expressing ROMK1. Specifically, a cell expressing ROMK1 can be selectively killed by providing to the cell an agent capable of binding ROMK1 which is conjugated to a cytotoxin.

The present invention further provides methods for generating chimerio or transgenic animals 1) in which the animal contains one or more exogenously supplied genes which are expressed in the same temporal and spatial manner as a member of the ROMK1 family of channel proteins, or 2) in which the member of the ROMK1 family of channel proteins has been deleted. Such chimeric and transgenic animals are useful in further elucidation the mechanisms of potassium channel function as well as their effect an animal physiology. These transgenic and chimerio animals are produced by utilization of techniques which are well known and well described in the technical literature.

The cloning of the gene for ROMK1, and the ROMK1 family of channel proteins also permits one to identify individuals with one or more defects in the genes encoding the ROMK1 family of channel proteins and correct the defect using gene therapy regimens known to the art. For example, the ROMK1 cDNA can be inserted in an expression vector such as, but not limited to, recombinant retroviruses (Collins, F. A., *Science* 256:774–779 (1992)). Cells exposed to this recombinant virus become infected and stably incorporate the new ROMK1 gene. In addition, there are vector-free approaches including encapsulating the ROMK1 DNA into various types of liposomes which are then taken up by cells or complexing the ROMK1 DNA to a protein normally taken up by the cell into which the new gene is to be transferred.

By the term "ROMK1 associated polypeptides" is intended such other distinct polypeptides as are intimately associated with the ROMK1 family of channel proteins. Although a single polypeptide type generally provides the structure for an ion channel pore [the pore itself may be a homomeric complex], this polypeptide may be intimately associated with other distinct polypeptides to form an ion channel complex (heteromeric complexes of polypeptides). For example, voltage gated $Na^+$ and $Ca^{2+}$ channel complexes are composed of three and five distinct protein subunits, respectively (Catterall, W. A., *Science* 242:50–61 (1988)) and the epithelial amiloride-sensitive $Na^+$ channel is a complex of 10 distinct subunits. These polypeptide subunits may be involved in the regulation of channel activity by regulating phosphorylation, G-protein binding, nucleotide binding, etc. Such subunits provide the target for the development of ROMK1 channel function modifying agents.

These other associated ion channel subunits can be identified during standard protein purification under non-denaturing conditions (Catterall, W. A. *Science* 242:50–61 (1988); Agnew et at., *Proc. Natl. Acad. Sci. USA* 77:639 (1980); Hartshorne et at., *J. Biol. Chem.* 259:1667 (1984))with the specificity of the protein complex identified by using an antibody to one of the subunits. Thus, an antibody to ROMK1 is used by one skilled in the art to identify ROMK1 associated subunits. Alternatively, one uses one or more of a variety of homobifunctional cross-linking reagents (Brenner et al., *Cell* 40:183–190 (1985); Oettgen et al., *Nature* 320:272–275 (1986))to link the ROMK1 protein to polypeptides with which it is in intimate contact and then immunoprecipitates the complex using an antibody to ROMK1. The cross-linked product is split into its individual polypeptides and the non-ROMK1 peptides identified and sequenced. Partial sequencing of the polypeptides [e.g., to provide a 15–20 mer fragment] is used to construct a nucleotide probe that is utilized to screen a cDNA library by high stringency hybridization. In this manner the genes encoding the ROMK1 associated polypeptides are cloned.

Once cloned, the genes for, and the ROMK1 associated polypeptides, may be utilized in like manner to the ROMK1 family of channel proteins, following procedures as described above.

Having now generally described the invention, the same will be understood by means of specific examples which are, however, not intended to be limiting unless otherwise specified.

EXAMPLES

We report here the cloning, functional characterization, and amino acid sequence of a $K_{ATP}$ channel cDNA, ROMK1, isolated by expression cloning. Patch clamp studies have recently demonstrated that the predominant potassium channels present in apical membranes of thick ascending limb epithelial cells are $K_{ATP}$ channels which are thought to mediate $K^+$ recycling in this nephron segment (Bliech et al., *Pflugers Arch.* 415:449 (1990); Wang et al., *Am. J. Physiol.* 258:F244 (1990)); similar channels in principal cells of the cortical collecting tubule may be involved in $K^+$ secretion (Wang et al., *J. Gen. Physiol.* 98:35 (1991); Wang et al., *Am. J. Physiol.* 259:F494 (1990)). Given these findings, the inner stripe of the outer medulla of rat kidney which contains an abundance of medullary thick ascending limb segments was used as a source of poly(A)+RNA for cDNA library construction. We have functionally expressed the cDNA in Xenopus oocytes and have shown that it is sufficient for encoding a $K^+$ channel which exhibits the basic properties of $K_{ATP}$ channels. The predicted protein with a calculated $M_r$ of 43 kDa shows marked structural divergence when compared to voltage-gated $K^+$ channel proteins. In contrast to these latter channels, the ROMK1 protein does not possess the characteristic structural motif of six membrane-spanning segments nor does it contain a typical S4 segment. Remarkably, however, the protein demonstrates the conservation of an amino acid segment which is homologous to the pore-forming H5 region of voltage-gated $K^+$ channels.

Expression Cloning of Complementary DNA

Two-electrode voltage clamping was used to study $Ba^{2+}$-sensitive potassium currents ($I_{K(Ba)}$) expressed in *Xenopus laevis* oocytes injected with poly(A)+RNA was isolated from the inner stripe of outer medulla (ISOM) of rat kidneys (FIG. 1). The criterion of $Ba^{2+}$-sensitivity was used as a means to selectively examine expressed potassium currents. RNA-injected oocytes displayed large inward $Ba^{2+}$-sensitive currents when compared with $H_2O$-injected oocytes at a membrane potential ($V_m$) of $-75$ mV with 50 mM external $K^+$ ($[K^+]_{ext}$) (FIGS. 1A, 1B). The $I_{K(Ba)}$ current expressed in RNA-injected oocytes was carried selectively by potassium ions as shown by the dependence of the observed reversal potentials ($E_{rev}$) for these currents on external potassium concentration (FIG. 1C). Size-fractionated mRNA with a size of $\sim$2-3 kb yielded a highly augmented mean inward $I_{K(Ba)}$sixteen-fold greater than that of $H_2O$-injected controls when injected into oocytes (FIG. 1D) and was therefore used to construct a directional cDNA library in the vector pSPORT1. RNA transcribed in vitro from pooled clones using T7 RNA polymerase was injected into Xenopus oocytes and tested for $I_{K(Ba)}$ currents using two-electrode voltage clamping. Functional screening of cRNA led to the identification of a 2.1 kb cDNA, ROMK1. Oocytes injected with ROMK1 cRNA ($\sim$0.3 ng/oocyte) exhibited a mean $1_{K(Ba)}$ of $-1408\pm179$ nA, n=10 (FIG. 1E) at $V_m = -60$ mV ($[K^+]_{ext}$=50 mM $K^+$). Characterization of the ionic selectivity of ROMK1 currents in $Na^+/K^+$ ion substitution experiments (FIG. 1F) using two-electrode voltage clamping demonstrated that ROMK1 encodes for a protein exhibiting high $K^+$ selectivity.

Characterization of ROMK1 Currents

Single channel recordings were obtained in oocytes injected with ROMK1 mRNA following vitelline membrane removal using standard patch clamp techniques to further characterize the properties of ROMK1 $K^+$ currents (FIG. 2). Inside-out patches excised from ROMK1 mRNA-injected oocytes displayed inwardly rectifying currents in the presence of symmetrical $K^+$ solutions (150 mM KCl) (FIGS. 2A, 2C). At negative membrane potentials, the amplitude of inward currents increased linearly with increasing hyperpolarization relative to $E_{rev}$($E_{rev}$=0 mV for symmetrical $K^+$ solutions). Inward currents showed a unitary slope conductance of 44 pS. In contrast, depolarizing membrane potentials resulted in outward currents with significantly smaller amplitudes. Moreover, the slope conductances of outward currents exhibited non-linear characteristics with increasing depolarization. Similar inwardly rectifying currents were also observed in the cell-attached patch configuration. The $K^+$ selectivity of these currents was confirmed by varying the pipette solution $K^+$ concentration ($[K^+]_{ext}$). Reversal potentials obtained with pipette solutions containing either 150 mM KCl or 50 mM KCl+100 mM NaCl were in complete agreement with the Nernstian predictions for $E_{rev}$ under these conditions (FIGS. 2B, 2C); the permeability ratio ($P_{Na}/P_K$) of 0.025 for these channels indicates high $K^+$ selectivity. Unlike voltage-gated $K^+$ channels, the open probability ($P_0$) for the expressed channels showed only slight voltage-dependence at membrane potentials in the physiological range; $P_0$ increased with depolarizing test potentials ($P_0$=0.40, 0;61, 0.74, 0.71 at $V_m = -90$, $-70$, $-50$, $-30$ mV, respectively). These electrophysiological characteristics are comparable to those of Type 1 $K_{ATP}$ channels, which have been characterized in pancreatic $\beta$-cells, cardiac myocytes, as well as skeletal and smooth muscle cells. Type 1 channels exhibit inwardly rectifying currents when exposed to symmetrical $K^+$ solutions, single channel conductances of $\sim$50-80 pS (symmetrical 140 mM $K^+$ solutions), relatively little voltage-dependence (Ashcroft et al., *Cellular Signalling* 2:197 (1990); Ashcroft, F. M., *Ann. Rev. Neurosci.* 11:97 (1988); Qin et al., *Am. J. Physiol.* 257:H1624 (1989)), and high $K^+$-selectivity (Ashcroft et al., *Cellular Signalling* 2:197 (1990)). Epithelial $K_{ATP}$ channels (classified as Type 3) present in renal tubular cells from the thick ascending limb of Henle and the conical collecting duct (Bliech et al., *Pflugers Arch.* 415:449 (1990); Wang et al., *Am. J. Physiol.* 258:F244 (1990); Wang et al., *Am. J. Physiol.* 259:F494 (1990)) have single conductances of $\sim$25-60 pS and share similar characteristics.

Figure 2A:
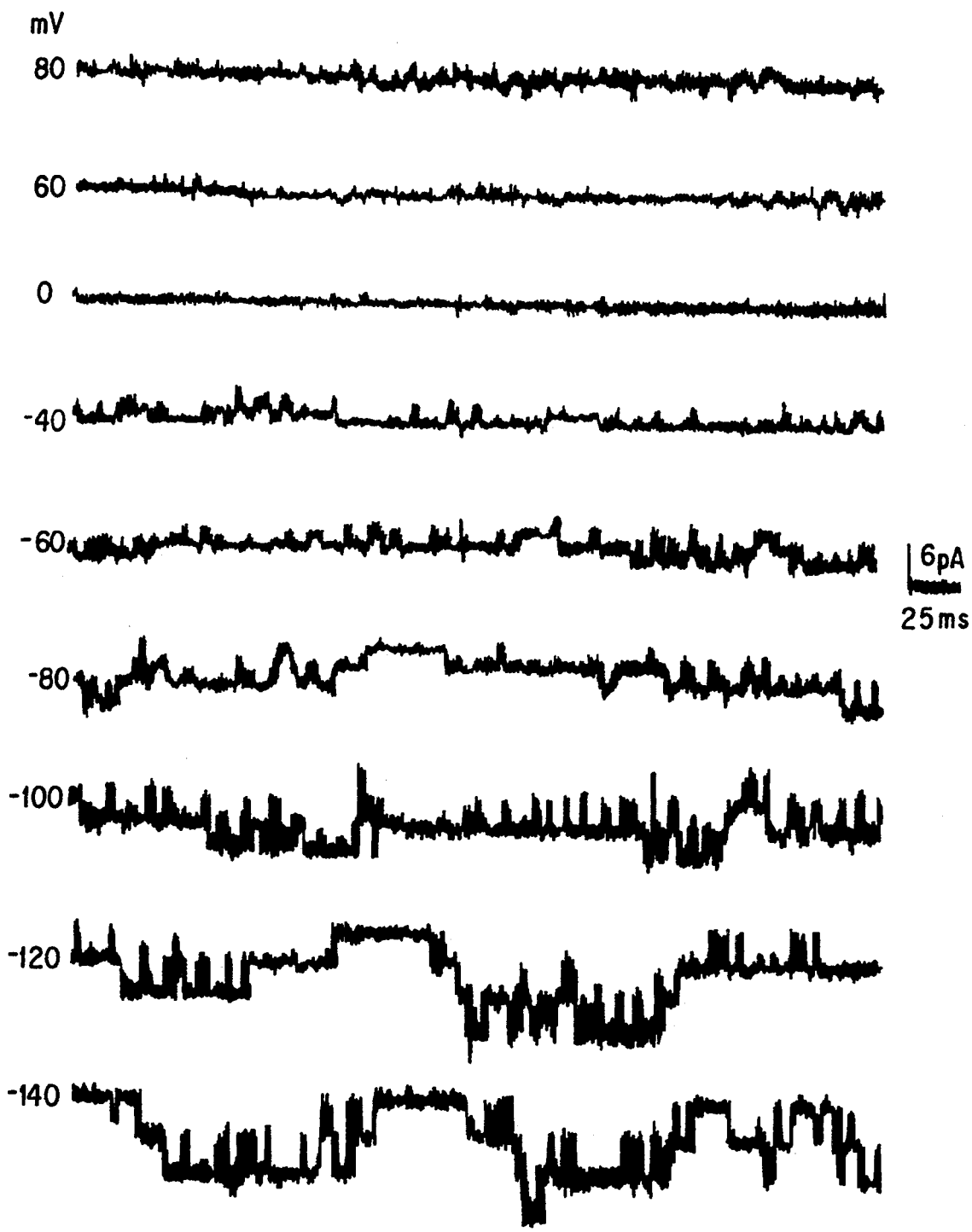
Figure 2B:
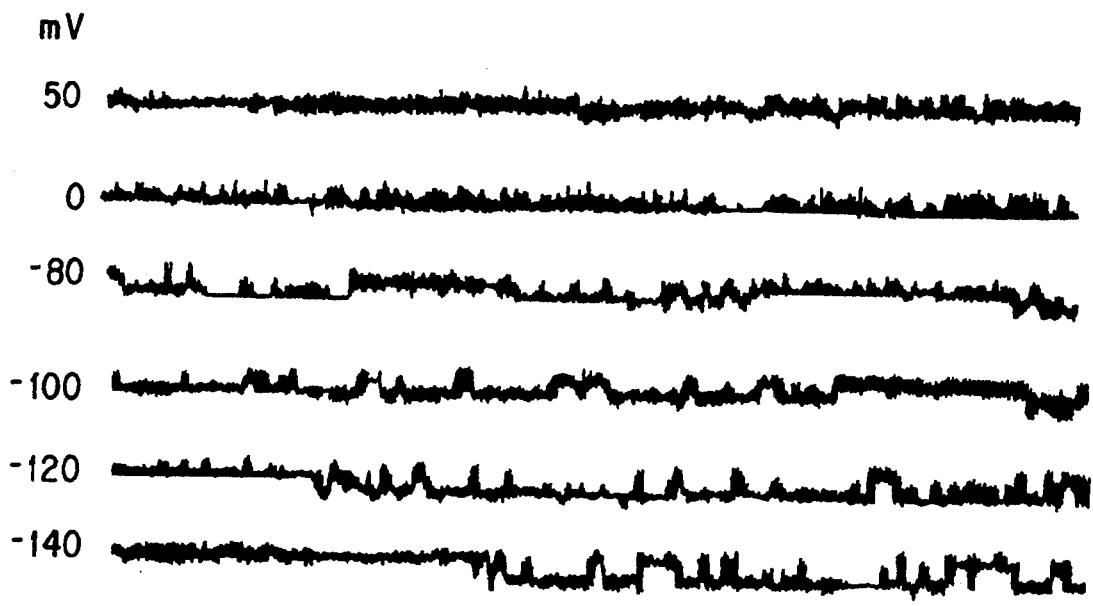
Figure 2C:
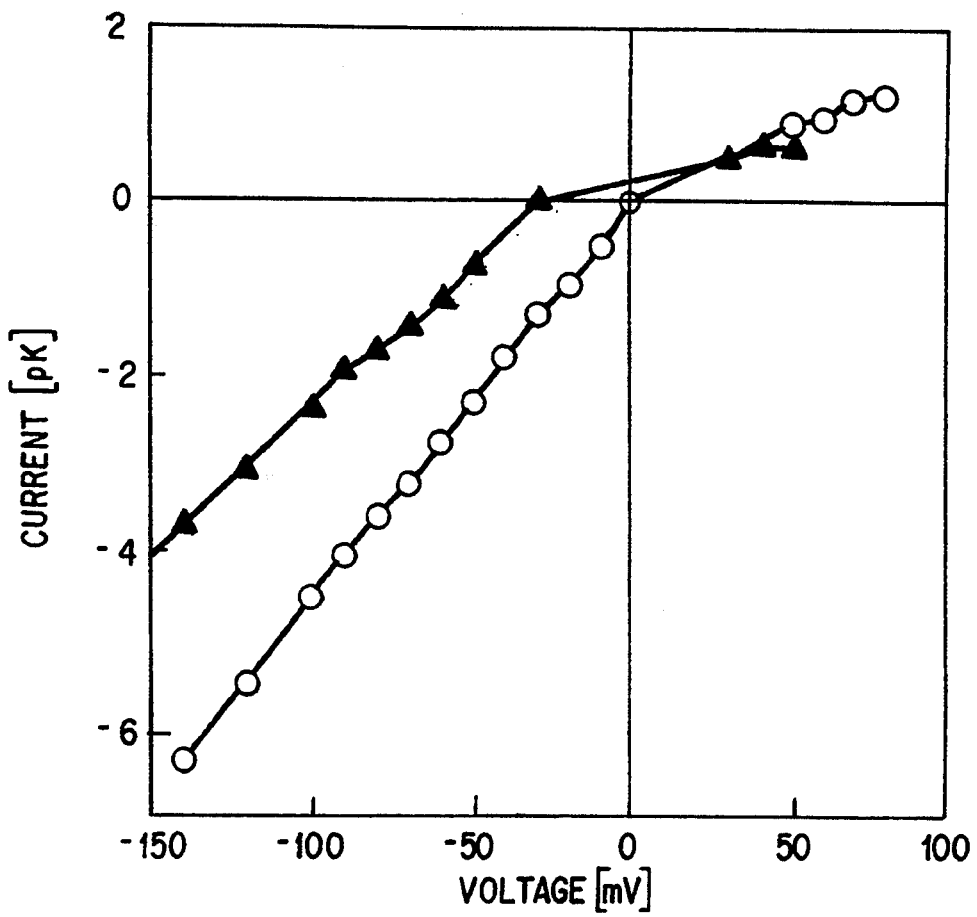
Figure 2D:
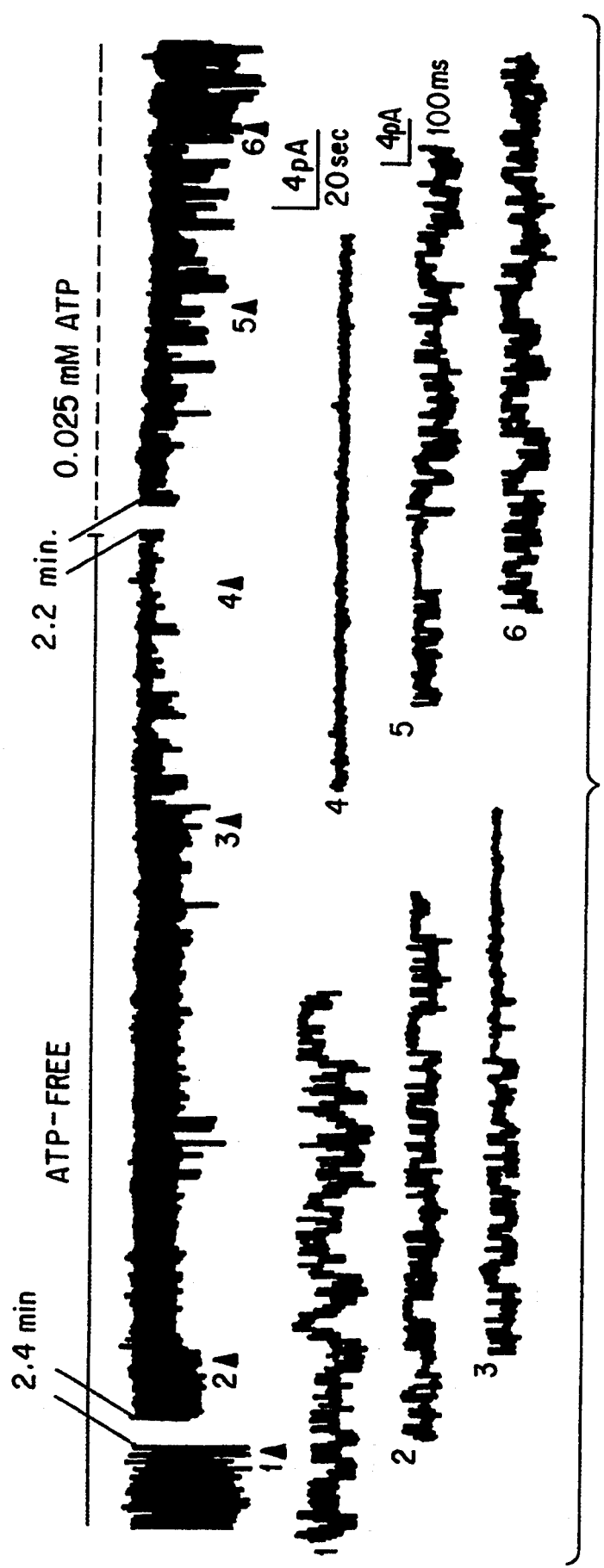
Figure 2E:
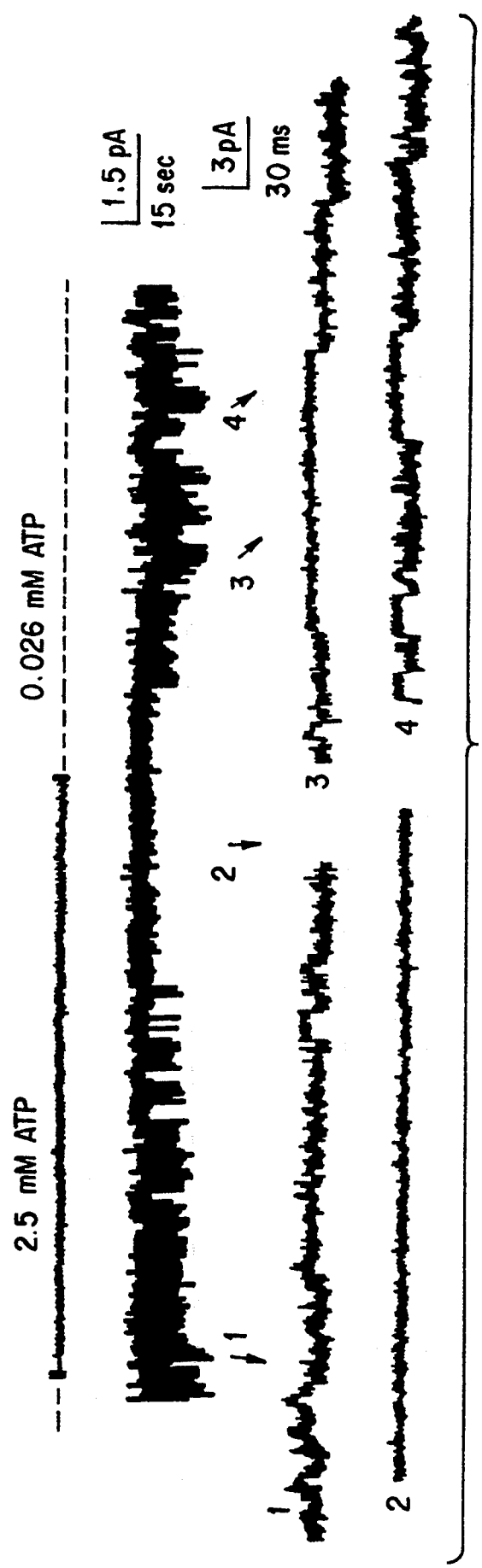

The effect of intracellular ATP on ROMK1 currents was also investigated using the inside-out patch configuration. Channel activity spontaneously decreased several minutes after removal of MgATP from the external bathing solution (0.025 mM→0 mM MgATP) (channel rundown) (FIG. 2D). Partial restoration of channel activity following complete channel rundown by the readdition of 25 $\mu$M ATP was observed in some cases. In contrast, channel activity was routinely maintained for 30 minutes or longer by excision of patches directly into a bath solution containing 25 $\mu$M MgATP. Application of high concentrations of ATP (1.0-2.5 mM), on the other hand, to the cytosolic face of inside-out patches initially excised into a bath containing 25 $\mu$M ATP reproducibly resulted in a rapid and marked inhibition of channel activity (FIG. 2E). This inhibition by ATP was found to be reversible as channel activity could be restored following wash-out of the high ATP-containing solution. Channels with these properties and electrophysiological characteristics were never observed in either cell-attached or inside-out patches from $H_2O$-injected control oocytes; in contrast, several channels of this type were typically active in patches from ROMK1 mRNA-injected oocytes. The incidence of ROMK1 channels in patches was 94% (63 of 67 patches) which was consistent with the high channel density observed in these experiments. This dual role of ATP as an inhibitor and as a requirement for the maintenance of channel activity has been well demonstrated for both Type 1 and renal Type 3 $K_{ATP}$ channels. In channels of both types, channel rundown rapidly occurs in excised membrane patches; this loss of channel activity is reversed or prevented, at least partially, by the addition of MgATP (Ashcroft et al., *Cellular Signalling* 2:197 (1990); Ashcroft, F. M., *Ann. Rev. Neurosci.* 11:97 (1988); Nichols et al., *Am. J. Physiol.* 261:H1675 (1991); Wang et al., *J. Gen. Physiol.* 98:35 (1991)). On the other hand, the channel activity of Type 1 and renal Type 3 $K_{ATP}$ channels (0.2-0.5 mM ATP) (Bleich et al., *Pflugers Arch.* 415:449 (1990); Wang et al., *J. Gen. Physiol.* 98:35 (1991)) is reversibly inhibited by intracellular ATP although that Ki for renal Type 3 $K_{ATP}$ channels (0.2-0.5 mM ATP) (Bleich et al., *Pflugers Arch.* 415:449 (1990); Wang et al., *J. Gen. Physiol.* 98:35 (1991)) is significantly higher than that for Type 1 channels in pancreatic $\beta$-cells ($\sim$10-20 $\mu$M) or in cardiac myocytes ($\sim$17-100 $\mu$M); Type 2 $K_{ATP}$channels which are found in central neurons (e.g., ventromedial hypothalamic nucleus), show less sensitivity to ATP with a Ki of $\sim$2-3 mM (Ashcroft et al., *Cellular Signalling* 2:197 (1990)).

Structural Features

The 2069 bp ROMK1 cDNA was bidirectionally sequenced yielding a single long open reading frame of 1,173 nucleotides downstream from three in-frame termination codons. This coding region encodes a protein of 391 amino acids with a calculated $M_T$ of 43 kDa (FIG. 3). The initiation codon was assigned to the first in-frame ATG which is contained within a strong Kozak initiation consensus sequence AGCAUGG (Kozak, M., *J. Biol. Chem.* 266:19867 (1991)). The size of this putative polypeptide was confirmed by in vitro translation experiments of ROMK1-specific mRNA using rabbit reticulocyte lysate which yielded a 45 kDa product by SDS polyacrylamide gel electrophoresis (FIG. 7). A 47 kDa glycosylated product obtained by translation in the presence of canine pancreatic microsomes is in agreement with the single glycosylation site predicted for the putative protein (FIG. 7). A long 3'-untranslated sequence of 726 nucleotides follows the coding region and contains two polyadenylation signal sequences of the form ATTAAA (Manley, J. L., *Biochemica et Biophys. Acta* 950:1 (1988)). These hexanucleotides occur in close proximity to each other and are located upstream from a poly(A) tail.

Sequence comparison using the GenBank, European Molecular Biology Laboratory (EMBL) and SWIS-SPROT databases revealed no significant similarities. In fact, hydropathy analysis suggests a strikingly unique topology for ROMK1 unlike any potassium channel protein cloned to date, namely, the presence of only two major hydrophobic regions M1 and M2 (FIG. 4). When Kyte-Doolittle hydropathy plots of ROMK1 are compared with those of potassium channel proteins from the Shaker superfamily, the M1 and M2 hydrophobic peaks together with two peaks of lesser hydrophobicity (M0, H5) appear reminiscent of the peaks corresponding to the S4, S5, H5 and S6 segments in voltage-gated potassium channels. Sequence analysis, however, reveals that only the amino acid sequence associated with the third peak (H5), which is flanked by the M1 and M2 regions, shares extensive homology with known potassium channel regions. Importantly this amino acid segment is remarkably similar to the pore-forming H5 region of potassium channels (MacKinnon et al., *Science* 245:1382 (1989); MacKinnon et al., *Science* 250:276 (1990); Yellen et al., *Science* 251:939 (1991); Hartmann et al., *Science* 251:942 (1991); Yool et al., *Nature* 349:700 (1991)) (FIG. 5). It has been suggested that the channel pore in voltage-gated potassium channels consists of an eight-stranded β-barrel structure formed by the H5 segments from each of the four component polypeptides (Yellen et al., *Science* 251:939 (1991); Miller, C., *Science* 252:1092 (1991)). A comparison of ROMK1 and Shaker H5 sequences reveals 7 identical amino acids (28%) and 4 conserved substitutions (16%) in a segment of 25 amino acids. The degree of homology is greatest (59%) in a core of 17 amino acids within this region having 7 identical (41%) and 3 conserved (18%) amino acids. Interestingly, this amino acid core is also shared to a comparable degree by Eag (Warmke et al., *Science* 252:1560 (1991)) and Slo (Atkinson et al., *Science* 253:551 (1991)), the two major potassium channel structural proteins showing significant divergence from the Shaker family. In voltage-gated potassium channels this highly conserved segment within the H5 region, the P segment (Durell et al., *Biophys. J.* 62:238 (1992)) (delimited by residues 431 and 449 in the Shaker H4 channel), has been shown to form the ion conduction pathway (MacKinnon et al., *Science* 250:276 (1990); Yellen et al., *Science* 251:939 (1991)). Single amino acid substitutions introduced into this segment by site-directed mutagenesis result in loss of channel function (MacKinnon et al., *Neuron* 767 (1990)) or changes in single channel conductance and ion selectivity (Yool et al., *Nature* 349:700 (1991); Kirsch et al., *Biophys. J.* 62:136 (1992)). In ROMK1 two amino acid substitutions are notable. A valine residue at position 140 replaces a highly conserved threonine residue at the corresponding position in Shaker sequences. In Shaker B, introduction of a mutation, T441S (threonine to serine), at this position dramatically increased the $NH_4^+$ permeability ($P_{NH4}/P_K = 0.85$) of the mutant without reducing its ability to exclude $Na^+$ (Yool et al., *Nature* 349:700 (1991)). An identical mutation in Shaker IR resulted in a dramatic reduction in the binding affinity of intracellular $TEA^+$ (Yellen et al., *Science* 251:939 (1991)). Moreover, an isoleucine (Ile 142) in ROMK1 occupies a position (443 in Shaker A) which is associated with changes in the ratio of $Rb^+/K^+$ conductance as displayed by DRK1 and NGK2 (Kirsch et al., *Biophys. J.* 62:136 (1992)). The finding of an H5 region in ROMK1 suggests a common ancestry with other potassium channels. And yet, the degree of amino acid identity shared between ROMK1 and Shaker proteins within this region when compared to that exhibited by the most divergent members of the Shaker family (35-40%, excluding Eag and Slo (Swanson et al., *Neuron* 4:929 (1990); Wei et al., *Science* 248:599 (1990)) emphasizes the distinct nature of ROMK1.

Apart from the P segment that forms the ion permeation pathway, the remainder of the S5-S6 linker in Shaker proteins is believed to form the external vestibule surrounding the channel pore (MacKinnon et al., *Science* 245:1382 (1989); MaeKinnon et al., *Neuron*5:767 (1990); MacKinnon et al., *Science* 250:276 (1990); Yellen et al., *Science* 251:939 (1991)). Comparable regions in the M1-M2 linker of ROMK1 show significant differences. Positions immediately adjacent to the P segment (corresponding to residues 431 and 449 in Shaker A) which affect the ability of both external $TEA^+$ and charybdotoxin (CTX) to inhibit channel activity in Shaker proteins are occupied by serine (Ser 130) and phenylalanine (Phe 148) in ROMK1. Both amino acids might be expected to decrease the affinity of either toxins for ROMK1 based on results obtained for analogous substitutions in Shaker mutants (MacKinnon et al., *Neuron* 5:767 (1990); MacKinnon et al., *Science* 250:276 (1990)). Replacement of threonine 449 in Shaker H4 by tyrosine and valine decreased channel sensitivity to CTX and $TEA^+$, respectively; channel affinity for both toxins was also reduced by substituting an asparagine for aspartic acid at position 431. On the other hand, the glutamic acid residues at positions 123 and 151 in ROMK1 would be expected to favor the binding of CTX specifically given the demonstrated electrostatic influence exerted by negatively charged residues located in similar positions near the external mouth of the Shaker H4 pore (MacKinnon et al., *Neuron* 5:767 (1990)).

ROMK1 also possesses a single potential N-linked glycosylation site at position 117 which is consistent with the predicted extracellular location of this segment. Interestingly, this glycosylation site occurs within a cluster of four proline residues which potentially may form a loop-like structure. Putative N-linked glycosylation sites are also present in the analogous S5-P links of Sha12, mSha1, and Eag channel proteins; like ROMK1, the two sites in the Eag segment also occur in a short stretch of amino acids containing several proline residues.

Of equal significance to the presence of an H5 region in ROMK1 is the remarkable absence of regions corresponding to the S1, S2, S3 and S4 segments present in all K+, Na+, and Ca$^{2+}$ voltage-gated ion channels. The absence of a typical S4 segment is particularly noteworthy. The highly conserved S4 segment is thought to form the voltage sensor in these channels (Catterall, W. A., *Science* 242:50 (1988); Papazian et al., *Nature* 349:305 (1991); Liman et al., *Nature* 353:752 (1991)). Using the ROMK1 H5 region as a reference point for alignment, the minor hydrophobic peak, M0, which would be expected to correspond to the S4 segment shows no characteristic S4 motif of repeating positively-charged residues at every third position (FIG. 6). Of the seven potential sites for basic residues in Shaker channel S4 sequences, every other of these sites is occupied by an uncharged residue (Phe, Thr, Trp) in the M0 segment of ROMK1, and two of the remaining four sites are occupied by negatively-charged amino acids. The M0 sequence contains only two positive charges in appropriate positions. It is possible that these substitutions may account for the relative lack of voltage-dependence exhibited by ROMK1 gating if the M0 segment represents an S4 region counterpart. The Shaw channel which displays significantly less voltage-sensitivity than other shaker channels may be analogous. The S4 segment of this channel contains only four positive charges, and two negative charges are present in positions that would be typically occupied by positive charges in other Shaker channels (Wei et al., *Science* 248:599 (1990)). Overall, the M0 region displays limited homology with K+ and Na+ channel S4 regions (36% with Shaker A, 24% with Na+ brain I, 4th domain).

In view of the inhibitory effect of ATP on ROMK1 channel activity, the amino acid sequence was also examined for nucleotide-binding motifs. Many but not all ATP-binding proteins contain an amino acid motif representing a phosphate-binding loop (P-loop) which has been suggested to be the only known region of homology common to all ATP/GTP-binding protein superfamily members (Saraste et al., *TIBS* 15:430 91990)). Furthermore, it often has been found that this Walker Type A consensus motif, GX$_4$GKX$_7$(I/V) as initially proposed (Walker et al., *EMBO J.* 1:945 (1982)), adopts distinct characteristics in individual protein families (e.g. GXPGXGKGT for adenylate kinases) (Saraste et al., *TIBS* 15:430 91990)). In ROMK1, a single motif of this type occurs following the M2 region (FIG. 3) in a segment with predicted secondary structure (small β-sheet—turn containing Gly 228 and Lys 229-α-helix) not unlike that (small β-sheet—turn -α-helix) predicted for phosphate-binding loops in adenylate kinase and some other ATP-binding proteins (Chin et al., *J. Biol. Chem.* 263:11718 (1988)). A number of these latter proteins also share a less conserved Walker Type B sequence (Walker et al., *EMBO J.* 1:945 (1982)), (H/K/R)X$_{5-8}$ΦχΦ$_2$(D/E) (Φ=hydrophobic residue) (Chin et al., *J. Biol. Chem.* 263:11718 (1988)) which is predicted to form a hydrophobic β-strand ending with a negatively charged residue. A candidate β-strand segment, VVFLD, is located the expected distance away from the P-loop motif toward the C-terminus in ROMK1. No homology was found, however, between the region containing these sequences in ROMK1 and the nucleotide-binding domains of ATP-binding cassette (ABC) superfamily members which include the CFTR protein (Hyde et al., *Nature* 346:362 (1990)). Taken together, these putative motif sequences in ROMK1 would predict a single ATP-binding site per polypeptide. A number of potential phosphorylation sites (Pearson et al., *Methods Enzymol.* 200:62 (1991)) for protein kinase C and cAMP-dependent protein kinase occur in close proximity to this nucleotide binding site. In addition, a high density of basic amino acids is also clustered near this site; all of the sixteen charged amino acids occurring in the segment delimited by residues 181 and 232 are positively charged.

Discussion

Patch clamp recordings of excised inside-out patches from injected Xenopus oocytes demonstrate that mRNA derived from ROMK1 cDNA alone is sufficient for the expression at high levels of a potassium channel that exhibits the basic characteristics of ATP-sensitive potassium channels. The topology of the ROMK1 protein suggested by local hydropathy analysis is strikingly novel and represents a major departure from the basic structural design of six membrane-spanning segments characteristic of the superfamily of voltage-gated and second messenger-gated ion channels (Jan et al., *Cell* 69:715 (1992)). Interestingly, however, ROMK1 shares specific structural features with other potassium channels which provides evidence for a common origin.

We propose that segments M1 and M2 are membrane-spanning and flank the pore-forming H5 region of ROMK1. The conformation of this latter region is likely to closely resemble that of Shaker channel H5 regions given the remarkably tight structural constraints in these segments as demonstrated by the effects of even subtle single amino acid substitutions on pore function. It is reasonable, then, that the channel formed by ROMK1 proteins is at minimum a tetrameric complex as in the case of Shaker channels. Also by analogy to voltage-gated potassium channels, glutamic acid residues (Glu 123 and Glu 151) may form a ring of negatively charged residues in the external vestibule of the ROMK1 pore composed of the M 1-P and P-M2 linkers. The only predicted glycosylation site for ROMK1 (Asn 117) is consistent with the extracellular location of the M 1-P linker. In contrast, both the highly charged hydrophilic N-terminal and C-terminal segments of the protein are probably cytoplasmic. The topology of the amphipathic M0 segment is unclear. Both the absence of a hydrophobic signal sequence and the predominance of positively-charged residues in the N-terminal segment (Hartmann et al., *Proc. Natl. Acad. Sci. USA* 86:5786 (1989)) would suggest that this end of the protein is located in the cytoplasm therefore making it unlikely that M0 spans the membrane completely. However, given the homology of the M0 sequence to Shaker S4 sequences, there remains the possibility that M0 interacts with the membrane in some manner. If the M0 segment were to fulfill a structural requirement in the protein, the modest voltage-dependence of ROMK1 gating would be consistent. In fact, S4-like sequences have been found in cyclic nucleotide-activated channels (Kaupp et al., *Nature* 342:762 (1989); Dhallan et al., *Nature* 347:184 (1990)) which are not voltage-gated. It has been proposed that the S4 segment arose in an ancestral channel and serves an essential structural function, apart from its role as a voltage-sensor, in the underlying core architecture of ion channels (Jan et al., *Nature* 345:672 (1990)). A similar argument may be relevant to the M0 region in ROMK1.

In the recently revised model of voltage-gated potassium channel structure proposed by Durell and Guy (Durell et al., *Biophys. J.* 62:238 (1992)), the Shaker channel is postulated to be composed of an outer ring of sixteen α-helices (segments S1, S2, S3 and S5), a middle ring of eight α-helices (segments S4 and S6), and an innermost β-barrel structure composed of P segments. The ROMK1 channel protein which has a maximum of three putative transmembrane segments would clearly have a different structure given its lack of regions corresponding to segments S1, S2, and S3. One possible model would consist of a β-barrel of P segments supported by a surrounding framework of eight transmembrane segments (M 1 and M2). The marked structural differences exhibited by ROMK1 would suggest that the ancestral gene encoding for this channel diverged early on during evolution from genes encoding voltage-gated and cyclic nucleotide-gated ion channels. Interestingly, it has been recently suggested that members of a superfamily of putative channel proteins (Baker et al., *Cell* 60:185 (1990)) which have six putative transmembrane segments and which may form tetrameric complexes (lens fibre major intrinsic protein (MIP), Drosophila neurogenic gene bib, *E. coli* glycerol facilitator (glpF), and soybean nodulin 26 (nod26)) may have evolved by the gene duplication of a single structural motif containing three membrane-spanning segments (Wistow et al., *TIBS* 16:170 (1991)).

The primary structure of ROMK1 also provides a possible insight into the role of ATP in regulating channel activity. The inhibition of $K_{ATP}$ channels by intracellular ATP is generally felt to result from the binding of ATP to a channel regulatory site(s) without the need for hydrolysis (Ashcroft et al., *Cellular Signalling* 2:197 (1990); Nichols et al., *Am. J. Physiol.* 261:H1675 (1991); Nichols et al., *J. Gen. Physiol.* 94:693 (1989)), although alternative models have been proposed (Ribalet et al., *J. Gen. Physiol.* 94:693 (1989)). In ROMK1, a single putative ATP-binding site identified by a Walker Type A nucleotide binding motif occurs in the long cytoplasmic stretch of amino acids following M2 in a region with predicted α-helical and β-sheet structure. The relative position of the nucleotide-binding site immediately following the hydrophobic domains of ROMK1 is similar to that of the single cyclic nucleotide-binding site in cAMP- and cGMP-gated channels. Moreover, these latter channels and $K_{ATP}$ channels both share steep nucleotide-dependent gating kinetics with Hill coefficients of about 2 (Kaupp et al., *Nature* 342:762 (1989); Nichols et al., *Biophys. J.* 60:1164 (1991)). A recent kinetic model for the $K_{ATP}$ channel, which features the sequential binding of ATP to multiple sites, suggests that the channel consists of four monomers with each monomer containing a single ATP-binding site (Nichols et al., *Biophys. J.* 60:1164 (1991)). This would be consistent with a tetrameric model of the ROMK1 channel which would predict a total of four ATP-binding sites. Likewise, the cGMP-gated channel, which has been found to be cooperatively activated by three or more cGMP molecules, is thought to be a homo-oligomeric complex with each component having a single cGMP-binding site (Kaupp et al., *Nature* 342:762 (1989)); evidence suggests that cyclic nucleotide-gated channels share a common structure with Shaker channels (Jan et al., *Nature* 345:672 (1990)).

On the other hand, the loss of KATP channel activity in isolated membrane patches (channel rundown) is at least partially reversed by MgATP but not by nonhydrolyzable analogues which suggests a role for phosphorylation in maintaining channel activity (Ribalet et al., *J. Gen. Physiol.* 94:693 (1989); Takano et al., *Am. J. Physiol.* 258:H45 (1990); Fiondlay, I., *Pflugers Arch.* 410:313 (1987)). Protein kinases A and C (Ribalet et at., *J. Gen. Physiol.* 94:693 (1989); Wolheim et at., *EMBO J.* 7:2443 (1988); De Weille et al., *Proc. Natl. Acad. Sci. USA* 86:2971 (1989)) have been found to modulate $K_{ATP}$ channel activity in different cell types. Likewise, the regulation of channel activity by PKA, PKC, and endogenous protein kinases has been demonstrated for both delayed rectifier (Walsh et al., *Science* 242:67 (1988); Rehem et al., *Biochemistry* 28:6455 (1989); Busch et al., *Science* 255:1705 (1992)) and $Ca^{2+}$-activated potassium channels (Reinhart et al., *J. Neurosci.* 11:1627 (1991); Chung et al., *Science* 253:560 (1991)). The presence of several potential phosphorylation sites for protein kinases A and C near the putative ATP-binding site in the ROMK1 protein is therefore intriguing. Clustering of multiple phosphorylation sites to a specific cytoplasmic domain has been noted in the α subunit of the rat brain $Na^+$ channel (Rossie et at., *J. Biol. Chem.* 262:17530 (1987)), in subunits of some ligand-gated ion channels (e.g., muscle and neuronal acetylcholine receptors (AChR), γ-aminobutyric acid (GABA) and glycine receptors) (Swope et al., *FASEB J.* 6:2514 (1992)), and in the R domain of the cFTR protein (Riordan et al., *Science* 245:1066 (1989)). In ROMK1, the apparent close association of phosphorylation sites and the putative nucleotide-binding sites raises the possibility that both types of sites may exert an effect on or participate in a common mechanism affecting channel opening and closure. In the "ball and chain" model of inactivation initially proposed for $NA^+$ channels (Armstrong et al., *J. Gen. Physiol.* 70:567 (1977)), the movement of a cytoplasmic domain results in the occlusion of the ion channel pore and therefore channel inactivation. Such a mechanism has been demonstrated in Shaker channels involving an N-terminal segment consisting of a cluster of positively-charged amino acids and a hydrophobic domain (Hoshi et al., *Science* 250:533 (1990); Zagbotta et al., *Science* 250:568 (1990)); an analogous role has been proposed for the highly charged R domain of the CFTR protein (Riordan et al., *Science* 245:1066 (1989)). The finding that cytoplasmic proteolytic treatment of Shaker and $NA^+$ channels either disrupts or slows inactivation is therefore consistent with the role of a cytoplasmic domain in channel inactivation. Similarly in pancreatic β-cell $K_{ATP}$ channels, internal trypsin treatment results in an increase in channel activity, as well as, a reduction in sensitivity to inhibition by ATP (Trube et al., in *Secretion and Its Control*, G. S. Oxford and C. M. Armstrong, Eds. (Rockefeller University Press, New York, 1989), vol. 44, pp. 84–95.). A potential candidate for such an inactivation domain in ROMK1 is the highly-charged cytoplasmic segment following M2 (residues 181–232) which contains the putative phosphorylation sites and P-loop. Other possibilities include the N-terminal (residues 1-57) and C-terminal (residues 331-391) segments in which 35% and 39%, respectively, of the amino acids are charged. All three clusters of potential trypsin sites in ROMK1 overlap these three amino acid segments. The knowledge of the ROMK1 amino acid sequence enables the design of experiments which address these issues and many others.

What is claimed:

1. An isolated nucleic acid molecule encoding a peptide consisting essentially of the amino acid sequence depicted in Sequence ID No. 2.

2. The isolated nucleic acid molecule of claim 1 wherein said sequence consists essentially of the nucleotide sequence depicted in Sequence ID No. 1.

3. The isolated nucleic acid molecule of claims 1 or 2 wherein said sequence further consists essentially of a vector selected from the group consisting of plasmids, phage, retrovirus, baculovirus and integration elements.

4. The vector of claim 3 wherein said vector is an expression vector.

5. An isolated nucleic acid molecule, which is capable of hybridizing to the isolated nucleic acid molecule of claims 1 or 2, wherein said hybridization occurs at about 5°–65° C. and in 5X SSPC and 50% formamide or equivalent hybridization conditions thereto.

6. A method of isolating the nucleic acid molecule of claim 5 comprising the steps of:

a) contacting a genomic or cDNA library with a probe comprising the sequence depicted in Sequence ID No. 1;

b) identifying sequences within said library which are capable of hybridizing to said probe, and c) purifying said sequence, wherein said hybridization occurs at about 50°–65° C. in about 5X SSPC and 50% formamide or equivalent hybridization conditions thereto.

7. The method of claim 6 wherein said probe is detectably labeled.

8. A method of using the isolated nucleic acid molecule of sequence ID No. 1, or a sequence which hybridizes under stringent condition to said sequence ID No. 1, to produce a peptide consisting essentially of the amino acid sequence of Sequence ID No. 2, comprising the steps of:

a) transforming a host with a DNA sequence capable of encoding said peptide, b) incubating said host under conditions which allows said sequence to be express; and c) isolating said peptide from said host.

9. The method of claim 8 wherein said DNA sequence comprises the nucleotide sequence of Sequence ID No. 1.

10. The method of claim 8 wherein said host is selected from the group consisting of bacteria, yeast, fungi, mammalian cells, plant cells, and insect cells.

* * * * *

UNITED STATES PATENT AND TRADEMARK OFFICE
CERTIFICATE OF CORRECTION

PATENT NO. : 5,356,775
DATED : October 18, 1994
INVENTOR(S) : Steven C. Hebert, et al It is certified that error appears in the above-indentified patent and that said Letters Patent is hereby corrected as shown below:

Column 1, before "FIELD OF THE INVENTION" insert the following text:
STATEMENT OF GOVERNMENT RIGHTS IN THE INVENTION
This invention was made with government support under Grant Nos. NIH 2 Rol DK37605 and NIH NRSA 5 F32 DK08487. The government has certain rights in this invention.--

Signed and Sealed this

Fourteenth Day of March, 1995

*Attest:*

BRUCE LEHMAN

*Attesting Officer*     *Commissioner of Patents and Trademarks*